(12) United States Patent
Cramer et al.

(10) Patent No.: US 7,860,657 B2
(45) Date of Patent: Dec. 28, 2010

(54) FORWARD SYNTHETIC SYNTHON GENERATION AND ITS USE TO IDENTIFY MOLECULES SIMILAR IN 3 DIMENSIONAL SHAPE TO PHARMACEUTICAL LEAD COMPOUNDS

(76) Inventors: Richard D. Cramer, 7 Likely Pl., Santa Fe, NM (US) 87508; Robert Jilek, 1204 Golden Harvest Dr., St. Peters, MO (US) 63376

( * ) Notice: Subject to any disclaimer, the term of this patent is extended or adjusted under 35 U.S.C. 154(b) by 512 days.

(21) Appl. No.: 11/728,727

(22) Filed: Mar. 26, 2007

(65) Prior Publication Data

US 2008/0172216 A1 Jul. 17, 2008

Related U.S. Application Data

(60) Provisional application No. 60/785,947, filed on Mar. 24, 2006.

(51) Int. Cl.
*G06F 7/00* (2006.01)
(52) U.S. Cl. .............................. 702/19; 702/20; 702/29; 703/11; 707/102
(58) Field of Classification Search ....................... None
See application file for complete search history.

(56) References Cited

U.S. PATENT DOCUMENTS

| 5,025,388 | A | 6/1991 | Cramer ........................ 700/293 |
| 5,307,287 | A | 4/1994 | Cramer ........................... 703/2 |
| 6,185,506 | B1 | 2/2001 | Cramer ........................... 506/8 |
| 6,240,374 | B1 | 5/2001 | Cramer ........................... 506/8 |
| 7,096,162 | B2 | 8/2006 | Cramer ........................... 703/1 |
| 7,136,758 | B2 | 11/2006 | Patterson ....................... 702/19 |
| 7,184,893 | B2 | 2/2007 | Cramer ......................... 702/19 |
| 7,329,222 | B2 | 2/2008 | Cramer ........................... 506/8 |
| 7,330,793 | B2 | 2/2008 | Cramer ......................... 702/19 |
| 2003/0220716 | A1 | 11/2003 | Mydlowec ................... 700/268 |
| 2005/0177280 | A1 | 8/2005 | Almstetter ................... 700/266 |

OTHER PUBLICATIONS

Todd "Computer-aided organic synthesis" Chem. Soc. Rev., 2005, 34, 247-266 Feb. 8, 2005.
Koca, A mathematical model of realistic contitutional chemistry, A synthon approach, II: The model and organic synthesis. Journal of Mathematical Chemistry, vol. 3, No. 1 / Jan. 1989.
Matyska et al., "A Computer Program for Organic Synthesis Design Based on Synthon Model of Organic Chemistry", J. Chem. Inf. Comput. Sci. 1991, 31, 380-386 (1991).

*Primary Examiner*—Mary K Zeman
(74) *Attorney, Agent, or Firm*—Laurence Weinberger

(57) ABSTRACT

A forward synthetic method is described that utilizes recursive application of established organic chemical reactions to derive more complex synthons from available reagents than are available from the reagent synthons themselves. The product of each reaction serves as the starting point for further reactions thereby permitting the generation of multiple complex molecular structures. This synthon generation procedure typically yields 20 ? 30 new structures within the limits of easily accessible syntheses based upon each starting reagent. More complex syntheses yield even more structures. The generated synthons are characterized with a molecular structural descriptor possessing a neighborhood property and can be further characterized with features. The synthons are searched for three dimensional shape and feature similarity to molecular fragments derived from query molecules, typically pharmacological molecules of interest. Identified synthons can be assembled into molecules possessing the same three dimensional shape and likely activity as the molecule of interest.

27 Claims, 15 Drawing Sheets

FORWARD SYNTHETIC SYNTHON GENERATION AND ITS USE TO IDENTIFY MOLECULES SIMILAR IN 3 DIMENSIONAL SHAPE TO PHARMACEUTICAL LEAD COMPOUNDS

Benefit of U.S. Provisional Application No. 60/785,947 filed on Mar. 24, 2006 is hereby claimed.

A portion of the disclosure of this patent document contains, material that is subject to copyright protection. The copyright owner has no objection to the facsimile reproduction by anyone of the patent document or the patent disclosure, as it appears in the U.S. Patent and Trademark Office, but otherwise reserves all copyright rights whatsoever.

Accompanying this written patent document is a CD-ROM computer program listing appendix containing the computer code necessary to practice the described invention. The software code on the CD-ROM computer listing appendix is incorporated and made part of this patent document. In Section IV.G below, each file on the CD-ROM computer program listing appendix is identified by its name, its size in bytes, and its date of creation.

I. BACKGROUND OF THE INVENTION

A. Field of the Invention

This invention relates generally to a computer implemented method for expanding the range/diversity of synthesizable chemical structures that can be searched for three dimensional shapes similar in shape to molecular fragments of known pharmacologically interesting molecules. More specifically, a forward synthetic method is described that utilizes recursive application of established organic chemical reactions to derive synthons from available reagents. The generated synthons are characterized with a molecular structural descriptor possessing a neighborhood property and searched for three dimensional shape similarity to molecular fragments derived from query molecules. Identified synthons can be assembled into molecules possessing the same three dimensional shape as the pharmacological molecule of interest.

B. Description of Related Art

1. Computer-Aided Synthesis:

"Pharmacological Chemical space," the distinct structures with a molecular weight less than approximately 1000 Daltons and in which the bonds to every atom obey standard valency rules, numbers over $10^{40}$ molecules, according to one serious estimate (Weininger)[1]. Most of these structures will never be synthetically available, either because the structure is too energetically unfavorable compared with its accessible decompositions or isomerizations, or more often because the structure is too difficult to synthesize compared to its potential benefits. The decision to synthesize any particular structure results from an assessment that the potential value of the structure is likely to exceed the costs of the attempt. Throughout this patent document, the term "costs" is intended to reference not only monetary expense, but also to reference the extent of time required, the level of effort required, and the consequences of diverting money, time, and effort away from other possible projects. Several computer-aided organic synthesis projects have had the estimation of such costs as their goal. Given a desired structure, the question was asked "how might this desirable (target) structure be synthesized and what is the cost?"

The original such project LHASA, begun in the late 1960's, introduced "retrosynthetic analysis" as the methodology for achieving this goal. As the name implies, retrosynthetic analysis proceeds in the opposite direction from actual laboratory synthesis, beginning by identifying the most promising building blocks ("synthons") and chemical reactions for producing the desirable end "target" structure, and then reapplying the same approach to each of the resulting synthons. Conceptually retrosynthetic analysis was a huge success, having become the major teaching paradigm for synthetic organic chemistry and winning a Nobel Prize in chemistry for its originator E. J. Corey. A recent article by Todd[2] traces the history and development of the field of computer-aided synthesis. LHASA was developed further over the years including extensions to deal with forward synthetic enzymatic reactions but it was never envisaged as a means to generate synthons that would not be utilized in a reaction sequence directed at a specific synthetic target. To date, there has not been a perceived need in the prior art to use computer-aided synthesis to generate a variety of synthons with the object of achieving structures with a broader range of three-dimensional shapes. Not surprisingly, computer-aided organic synthesis projects subsequent to LHASA have operated retrosynthetically, their only use of starting materials being as input to answer the question: "have we reached the desired synthetic target yet?"

2. Shape Based Comparison:

a. Molecules Viewed as Assemblies of Parts:

In pharmaceutical drug development, the situation frequently arises where it is desirable to make some alteration to a lead compound. The alteration may be simple or it might necessitate the replacement of significant parts of the molecule. In order to retain the biological specificity of the lead compound, any replacement part should have a similar three dimensional shape. When comparing the three dimensional shape of one molecule to another, in computational chemistry it is convenient to view the molecules as assemblies of constituent parts. Typically, a molecule is viewed as an assembly of fragments where the fragments are derived by severing bonds within the molecule in a consistent manner. Fragments are a useful way to deconstruct the three dimensional shape of molecules so that similarly shaped parts may be identified. Similarity of shape of the whole molecules (such as a lead compound and a possible alternate compound) can then be determined by comparing the shapes of the individual molecular fragments. A simple example would be two molecules A and B which could each be fragmented into two roughly similar parts: A1 and A2, and B1 and B2. The shape of A1 would be compared to the shape of B1. The shape of A2 would be compared to the shape of B2. Alternatively, rather than comparing fragments of two molecules, it may be desirable to compare fragments from a lead compound with molecular structures (fragments) derived from available reagents or which could be independently synthesized.

Computer representations of the fragmented parts of a lead molecule or fragments derived from available reagents or that could be independently synthesized each retain an open valence where they were or could be "attached" to form a whole molecule. This approach has two major advantages. First, the open valence provides a reference point that enables fragments to be commonly aligned. Alignment is necessary since shape similarity implies that the atoms of each fragment occupy similar positions in three dimensional space. Second, if the compared fragment does not share the same shape as the lead compound derived fragment (within some measure of similarity), it is unlikely that the substitution of the compared fragment for the fragment from the lead compound would produce an active compound. As will be seen below, this simple dissimilarity searching criteria can eliminate large numbers of possible fragments very quickly and permits very high search speeds through enormous fragment databases.

b. Advances in Validating Metrics:

While the goal of shape comparison existed in the prior art and a variety of shape descriptors were tried, no method was known that could validate whether a descriptor (molecular structural metric) described the three dimensional molecular shape in a manner that was biologically relevant. In this environment shape comparisons could be performed but one could not know if the results were meaningful. Over the past several years a new method of metric validation for use in drug discovery has become available which has opened up to searching, for useful and/or improved variations of pharmacological compounds, the large universe of possible organic chemical compounds. The fundamental keys to unlocking this possibility were disclosed in U.S. Pat. No. 6,185,506. The first key was the development of a methodology (the "Patterson Plot") for determining whether a molecular structural descriptor (metric) was "valid", that is; whether it described molecules in such a way that the descriptor values properly reflected the likely biological activity of the molecules. Of course, validity in this context reflects a high probability not a certainty. Once a validation methodology was known, available descriptors were evaluated and generally found wanting.

c. Development of Topomer Metric:

The second key was the development of a valid descriptor that properly reflected the three dimensional shape of molecular parts. As noted, a valid molecular structural shape descriptor had been an elusive goal of pharmacological research since it was understood that the three-dimensional shape of a ligand molecule had a great deal to do with the molecule's ability to bind to a receptor in a lock and key type arrangement. Previous work had focused on trying to determine which, of the thousands of possible conformations that a small molecule can attain, was likely to be the conformation that was critical for interaction with a receptor. Most methodological development in the 3D modeling of chemical structures for pharmacological research was aimed, quite understandably, toward greater physicochemical realism. In some approaches, statistical shape averages were employed, in others gross shape estimates were employed, while in others key pharmacophoric features were emphasized. Some successful approaches employed knowledge gained from x-ray structures of ligand-protein binding. However, the real world physicochemical reality is that biologically interesting molecules exhibit an intractable multiplicity of shapes and states. In practical applications, the various summarizations employed were so approximate as to perhaps be self-defeating. In addition, no general methodology was applicable across the broad range of chemical structures and activities.

The answer to discovering a valid descriptor that properly reflected the three dimensional shape of molecular parts turned out to be counter intuitive. Rather than trying to determine the most likely conformations of molecules, it was discovered that the alternative goal, consistency of alignment, rather than realism, in the positioning of similar structural features into similar regions of an arbitrary geometric space was the answer. The development of topomers, molecular fragments (molecular structures having an open valence [attachment bond] at least one position) aligned according to a deterministic set of rules that produce absolute configuration, conformation, and orientation, was taught in U.S. Pat. No. 6,185,506 and further extended in U.S. Pat. No. 6,240,374.

The method of defining the shape of the topomers so that useful shape comparisons could be made was adapted from the CoMFA procedure described in U.S. Pat. Nos. 5,025,388 and 5,307,287. In CoMFA, the steric fields surrounding molecules were demonstrated to be an effective and realistic determinant of the molecular shape of the molecules under consideration. Using a similar approach, steric fields around topomerically aligned molecule fragments were demonstrated to form a validated molecular structural descriptor. The disclosures of U.S. Pat. No. 5,025,388, U.S. Pat. No. 5,307,287, U.S. Pat. No. 6,185,506, and U.S. Pat. No. 6,240,374 and their attached software appendices are incorporated into this patent document as if fully set forth herein.

d. Topomer Based Shape Comparison:

The use of the steric fields around topomerically aligned fragments as a molecular structural descriptor (metric) permits the shapes of the fragments to be compared. Since the metric is valid, similar topomeric shapes of two fragments implies a high likelihood of similar biological activity. Shape searching using the steric fields of topomerically aligned fragments initially advanced the development of combinatorial libraries (U.S. Pat. No. 6,185,506). Subsequently, it was realized that the shapes of fragments derived from reagents used in combinatorial syntheses could be precomputed and stored in a virtual library along with other information such as the chemical reactions in which the reagents participated (U.S. Pat. No. 6,240,374). Given a query molecule with a known activity that could be broken into fragments, the shapes of those fragments (topomerically aligned and characterized with their steric fields) could be searched in the virtual library of molecular fragments to identify other chemical structures of similar shape that could be substituted for the query fragments and would have a high likelihood of having a similar biological activity. Topomer searching finds biological equivalent structures. More recently, it has been shown[3] that topomerically aligned fragments can be utilized in the CoMFA methodology to generate a valid CoMFA. The techniques of the present invention extend even further the usefulness of topomers.

II. SUMMARY OF THE INVENTION

The invention described in this patent document teaches a method of increasing the richness or diversity of molecular synthons that is not limited to the structures of the constituents (reagents) or products of combinatorial chemistry and that can be used in a topomer shape searching system. To this end, topomer shape similarity searching has been blended with a unique approach to computer-aided synthesis design. A computer-aided organic synthetic method provides for recursively generating the structure of complex synthons, which have at least one open valence, and that may be derived from available starting reagents by well established organic chemical reactions.

Each synthon is associated with a particular type of reactivity dependent upon the nature of its synthesis. The synthons exhibit a wide range of three dimensional shapes heretofore not easily accessible. Each generated synthon is aligned by a rule based topomeric procedure and its three dimensional shape characterized by the surrounding steric field (topomer metric). Each aligned synthon is further characterized by the presence of pharmacophoric features. The resulting molecular structural descriptor of each synthon is stored in a relational data base along with information on the synthetic route to its creation, its reactivity, and the costs associated with its synthesis. Additional information related to each synthon, including but not limited to reaction conditions or the commercial source of the starting reagents, may also be stored in the data base. The data on each synthon is easily retrieved from the data base including viewing of the route of synthesis. The three dimensional shapes, reactivities, and pharmaphcoric features of the synthons can be searched for similarity to the shape, reactivities, and pharmacophoric features of molecular fragments derived from query molecules, typically drug discovery lead molecules, to identify synthons having complementary reactivity and similar shape to the query fragments and which could be substituted for the query fragments to form an alternative drug like molecule likely possessing the same biological activity.

III. DESCRIPTION OF FIGURES

IV. DETAILED DESCRIPTION OF THE INVENTION

A. Computational Chemistry Environment

1. Software

Figure 1:
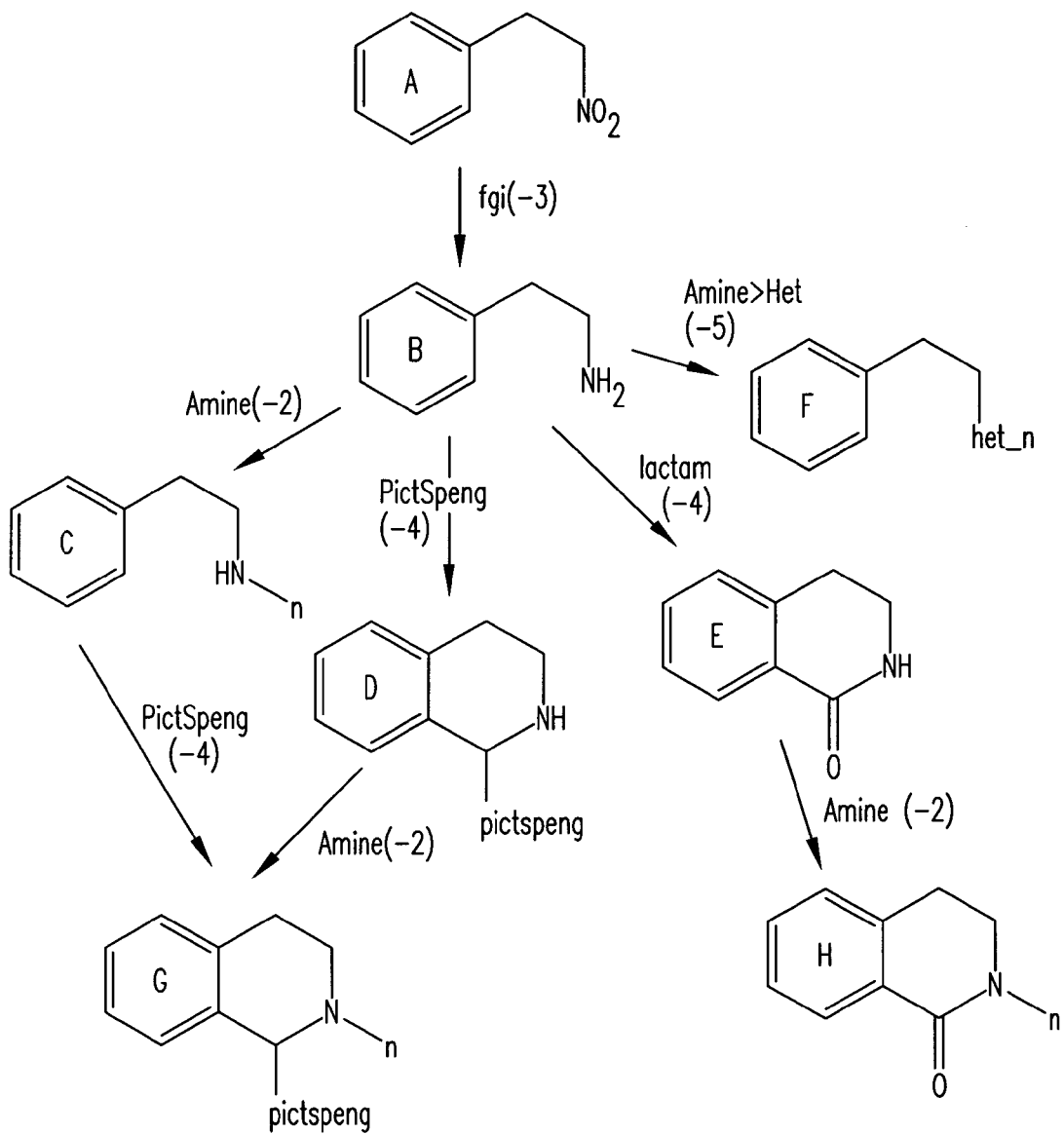
FIG. 1 shows several molecular structures including synthons which may be recursively generated by exemplary organic synthetic reactions.

Generally, all calculations and analyses to perform the method of the present invention, including but not limited to, generating forward synthetic routes, recursively generating synthons, characterizing synthons with valid metrics, fragmenting query molecules and characterizing the fragments with valid metrics, and searching for synthons having similar three dimensional shapes and pharmacophoric features to the fragments derived from query molecules, are implemented in a modern computational chemistry environment using software designed to handle molecular structures and associated properties and operations. For purposes of the present application, such an environment is specifically referenced. In particular, the computational environment and capabilities of the SYBYL and UNITY software programs developed and marketed by Tripos, Inc. (St. Louis, Mo.) are specifically utilized. Software with similar functionalities to SYBYL and UNITY are available from other sources, both commercial and non-commercial, well known to those in the art. The inventors use Oracle as a relational database. Other databases known to those in the art with similar relational capabilities may me used. Because the information generated by the invention described in this patent document is stored in a relational data base, different information can be retrieved and formatted as a user desires using well known data base query approaches.

Software to perform topomeric fragment alignments and compute their steric fields was disclosed as part of U.S. Pat. No. 6,185,506. Software to perform topomeric fragment alignments of chiral fragments and to generate and search a Virtual Library of molecular components was disclosed as part of U.S. Pat. No. 6,240,374. As will be quickly recognized by those skilled in the art, not all the software code provided in the cited patents is required to practice the method of the present invention. (As an example, code providing for the calculation of Tanimoto metric values is not required.) Updated software code to characterize topomers and features and that is unique to and required (in the computational environment specified herein) to practice the present invention is disclosed in the attached software appendices on the CD-ROM. Unless otherwise noted, all software references and commands in the following text and software appendices are references to functionalities contained in the SYBYL and UNITY software programs. As noted above, the entire disclosures of U.S. Pat. No. 5,025,388, U.S. Pat. No. 5,307,287, U.S. Pat. No. 6,185,506, and U.S. Pat. No. 6,240,374 including the software code which forms a part of each patent disclosure, are incorporated herein as if fully set forth.

2. Hardware

A general purpose programmable digital computer with a fast CPU, ample amounts of memory, hard disk storage, display screens and printer outputs is required for the implementation of this invention. In performing the methods of this invention, representations of thousands of molecules, molecular structures, and fragments as well as other data may need to be stored simultaneously in the random access memory of the computer or in rapidly available permanent storage. The inventors use an SGI four processor R16K server with each processor running at 700 MHz with 8 GMB of total RAM available to perform the topomer similarity computations in tandem with an Oracle server. As the size of the relational data base increases, a corresponding increase in hard disk storage and computational power and speed may be required.

Since a user of the method of the invention disclosed in this patent document can best understand and study the output of the synthetic generator and the computational shape analysis visually, especially given the enormous number and diversity of chemical structures analyzed, a display screen and system capable of visualizing and manipulating images of the three dimensional shapes is used. Chemists are generally some of the most visually oriented scientists when thinking about chemical structures, and the screen output of the synthetic generator and the computational analysis matches their visual approach. Alternatively, selected results can be either captured as screen images or printed out on hard copy.

B. Definitions

1. Fragment/Synthon: The terminology used to refer to a chemical structure having an open valence (attachment bond) at least one position has evolved over the course of the development of the methods described in U.S. Pat. No. 6,185,506, U.S. Pat. No. 6,240,374, and various U.S. patent applications still pending. In U.S. Pat. No. 6,185,506 it was noted that reactants (reagents) before their involvement in a chemical reaction will not have an open valence, but will have that valence position filled with an atom or atoms which are discarded during the reaction and not found in the final product. The fragment is that part of the reactant remaining along with the open valence after the discard of the atom or atoms from the valence position. Alternatively, using the terminology of U.S. Pat. No. 6,185,506, fragments are the molecular side chains derived from reactant molecules. Fragments by this definition may exist only transiently or not at all in an actual chemical reaction. However, for computational purposes, they can be handled directly. Note that even in U.S. Pat. No. 6,185,506 "fragment" has a different meaning when used in conjunction with the Tanimoto metric where "fragment" refers generally to a 2-7 atom piece of a larger complete molecule.

A chemical structure having an open valence (attachment bond) at least one position was referenced as both a fragment and as a "structural variation" when discussed in U.S. Pat. No. 6,240,374 in the context of combinatorial chemistry libraries. The term "structural variation" was used to connote that the chemical structures with the open valences were responsible for the structural variation in a combinatorially derived molecule. U.S. Pat. No. 6,240,374 also taught that molecules (query molecules) could be cut up (fragmented) into two or more fragments for purposes of doing shape comparisons between the structural variations and the molecular fragments. When the query molecule was cut for analytical purposes, each fragment by definition retained an open valence (attachment bond). Any part of a chemical structure which can be severed from the remaining structure so as to have one or more open valences (attachment bonds) can be considered as a fragment. As noted above, fragments are a useful way to deconstruct the three dimensional shape of molecules so that similarly shaped parts (synthons) may be identified.

For purposes of this patent document, the more general term "SYNTHON" recognized and utilized by organic chemists will be employed to refer to all the above cases and shall mean a representation of a chemical structure having an open valence (attachment bond) at least one position. Synthons can be derived from a reagent, from a synthetic reaction sequence, or from the fragmentation of a molecule. Synthons may be used to computationally assemble a whole molecule, or when appropriate through synthetic organic chemistry, to synthesize a whole molecule.

2. Multistep Intermediate: Multistep Intermediate shall mean an intermediate resulting from a synthetic organic chemical reaction starting with an available reagent and involving at least two synthetic steps.

3. Topomeric Metric: In U.S. Pat. No. 6,185,506 and U.S. Pat. No. 6,240,374 a molecular structural descriptor (metric) was described which consisted of the steric field values generated at all lattice points in a three-dimensional grid between a probe atom and a molecular fragment having a topomerically (rule-generated) conformation. At the time those patent documents were drafted, the term used to describe the metric was "topomeric CoMFA metric." Use of the term "topomeric" was utilized to reference the conformation of the fragment. Use of the term "CoMFA" was made to reference a field generated at all lattice points in a surrounding three-dimensional grid. At that time, the inventors had no idea that the steric and electrostatic field values about a topomerically aligned fragment could be utilized in a methodology with the previously developed CoMFA technology to yield a valid CoMFA model (as disclosed in pending application Ser. No. 09/825,448), and much less, that the term "topomeric CoMFA" would, in fact, be the useful descriptive name for that methodology. In this patent document, the term "topomeric CoMFA metric" is no longer used to refer to the metric consisting of steric fields about a topomerically aligned fragment. When the metric is referenced, it is referred to as the "TOPOMERIC METRIC", the metric consisting of the steric fields about a topomerically aligned fragment.

4. Topomeric Metric with Features: By the term "features" is meant the customarily identified classic pharmacophoric five feature classes: positive charge, negative charge, hydrogen-bond-donating, hydrogen-bond-accepting, and aromatic. The method of identifying and locating these features in a molecule or molecular fragment is well established in the art. Placing a fragment containing features into a topomeric alignment displaces the features from their three dimensional position in the non-aligned fragment. However, the presence or absence of the feature in the topomerically aligned fragment can be identified and the Cartesian coordinates of the feature or features determined and stored. The resulting molecular structural descriptor containing both the feature information and the steric fields is referred to as a topomeric metric with features.

5. Topomer Searching: The topomeric metric or the topomeric metric with features can be used to compare the shape of fragments. "Topomer searching" or equivalently, "topomerically searching", means the comparison of fragments for similarity of shape using the topomeric metric or the topomeric metric with features.

6. Synthon: Synthon shall mean a representation of a chemical structure having an open valence (attachment bond) at least one position.

C. Forward Synthesis of Complex 3D Structures

1. Expanded Range and Complexity

The virtual library of U.S. Pat. No. 6,240,374 permits searching through a huge expanse of chemical space estimated to be about $10^{13-14}$ possible structures. However, one current limitation of virtual library searching is that all the candidate structures must be products of some explicit, hence very short, combinatorial synthetic protocol. Most importantly, however, while there is much diversity of three dimensional chemical structure in commercially available reagents, that range of chemical structure diversity does not begin to compare with the range of three dimensional structural diversity found in pharmacological compounds. The majority of pharmacologically interesting molecules result from longer synthetic sequences or unique enzymatic processes that result in complex structural arrangements. Most pharmacologically interesting molecules (including natural products) were not and usually could not be synthesized by the short coupling sequences of combinatorial chemistry utilizing only commercially available reagents.

The present invention addresses the need to extend the range and complexity of available three dimensional chemical structures to approximate the diversity and complexity of pharmacologically interesting molecules. These structures may, in turn, be topomerically searched for similarity of shape to fragments derived from a query molecule. As an example of the utility provided by the synthon generator, a recent survey by the inventors of pharmacologically interesting molecules described in J. Med. Chem. indicated that approximately 75 percent of the molecular structures were represented by a small number of synthons generated by the synthetic generator connected by acyclic single bonds. The corollary to this finding is that the data base of synthetically generated synthons can be productively searched for combinations of synthons having similar shape to most structures of medicinal interest.

There are several reasons that fulfillment of this need is particularly important in the pharmaceutical arts. For example, it is often the case in drug development that compounds derived from a particular line of synthesis can not be used as pharmacologic agents: they may be too large to be easily absorbed, they may be toxic, they may not have a specific enough activity, or they may not be sufficiently potent. What is critically desired is to be able to accomplish a "lead hop"; that is, a switch to compounds with different chemical structures (typically resulting from different synthetic chemical reactions) that exhibit activity in the same biological system (receptor/enzyme) as the initial pharmacologic agent but that do not have the undesirable traits. To exhibit the same or similar biological activity, it is necessary for the lead hop compounds to have three dimensional shapes and pharmacophoric features similar to the initial pharmacologic agent.

Another example where it is desirable to extend the available range of complexity of structures is the situation where the structure of a drug effective at a given biological target is known and companies not owning the effective drug wish to develop new drugs for the same biological target while avoiding the patents covering structures of the known drug. What is desired is essentially a "lead hop" into a different patent area. Yet another example is the situation where, based on structure activity relationship (SAR) data, it is desirable to modify compounds of a given chemical series to improve their specificity or activity. These examples are not meant to be limiting, and those skilled in the art will readily appreciate the various applications of the methods described herein.

2. Novel Computer Aided Forward Synthesis

The major advance over the prior art enabled by the synthon generator disclosed in this patent document is that it is a synthetic route generator that works primarily in terms of explicit open valences, their generation, and their mutually reactive properties. Prior art commercially available reaction libraries are all based on complete structures with no open valances on either side of the reaction equation. Also, the synthon generator of the current invention differs from previous computer-aided organic synthesis techniques in two fundamental ways:

1) its operations proceed in the forward synthetic rather than the retrosynthetic direction, with the object of determining the structures that can be synthesized with given sets of building blocks and reactions; and 2) it permits assessment of the cost of synthetic routes to each synthon.

In order to implement the synthon generator of the present invention, use is made of the related technology of "reaction databases". These are databases which accumulate searchable literature reports of successful outcomes in applying individual reactions to particular structures. These databases are widely consulted by chemists to provide guidance on which "reaction conditions" (solvents, catalysts, temperatures, times, etc.) are most likely to work with other particular structures. However, in the prior art the entries in these reaction databases have never been linked together and applied to many starting materials in the manner of the current synthon generator invention.

Before the recursive synthon generator can operate, descriptions of the starting molecules upon which the generator will operate need to be specified. This data is input in a separate file available to the synthon generator. Once this data is entered, the synthon generator has all it needs to proceed.

3. Synthon Generation

The key realization behind the development of the present method was that two key types of information, synthon generation rules and synthon reactivities, could be provided outside of the restrictive formalism of an explicit virtual library as disclosed in U.S. Pat. No. 6,240,374. As a simple example, the lists of acyl and amino synthons and a combination rule that comprise an "amide" virtual library could equivalently be generated by the following three rules:

1) removal of an OH from RC(=O)OH generates an electrophilic synthon 2) removal of an H from an HN(R1)R2 generates a nucleophilic synthon 3) any nucleophilic synthon will readily form a bond to any electrophilic synthon Obviously the categories of electrophilic and nucleophilic synthons include many more structures than RC(=O)— and —N(R1)R2, so that a single "e-n" combination rule has efficiencies of generality. The enormous benefit of this reformulation of virtual chemistry is that synthon generation can become recursive. Each newly generated synthon can be reprocessed by the same set of synthon generation rules used to create it, thereby generating the desired arbitrary sequences of synthetic steps and producing an immense variety of three dimensional shapes. As will be discussed below, the complex range of structures represented by the synthons generated from arbitrary sequences of synthetic steps can then be topomerically characterized and searched for shapes similar to fragments derived from pharmacologically interesting molecules.

In the development of the synthon generator, the organic synthetic reactions employed were taken from the encyclopedic compilation of combinatorial chemistry references by Nicolaou[4]. Of course, the methods of the present invention are not limited to those reactions presently incorporated into the synthon generator, but can be expanded by any additional reactions desired. Presently available starting reagents were used. Again, additional reagents can be incorporated as desired. For the initial development of the synthon generator, reaction definitions were applied to reagents listed in commercial compendiums of available compounds. The reaction definitions were then applied recursively with each generated synthon, that is, each generated synthon is processed by the same synthetic reactions—being further used as a starting point for the next round of synthesis with the same set of reaction definitions. Essentially, the synthon generator of this invention applies arbitrary reactions to arbitrary reagents in synthetically reasonable ways according to known synthetic protocols.

In this manner some synthetic steps do not generate synthons while other steps may yield synthons identical to that produced by yet other pathways. Information on all generated synthons including those derived from different pathways is kept so that all synthetic routes to a synthon are known and available. Individual synthetic paths to any give synthon can be displayed for review by the user. In addition to the limitations imposed by available reactions and reagents, there are some practical constraints on the synthon generating method (how far a recursive sequence is permitted to advance). The two most important constraints being the size of the synthon and the cost of each synthetic reaction sequence.

Generally, at least three synthons will be assembled to form a new compound. If the synthons are limited to 15 or fewer heavy atoms (corresponding to a molecular weight in the range of 200) the final molecule will have a molecular weight of under 1000 which is generally considered necessary for a pharmaceutical compound. By "cost", as noted earlier, is meant the time and effort that must be expended to implement the sequence. Clearly, as more and more synthetic steps are required to reach a particular synthon, the cost of producing that synthon becomes greater. An additional constraint is imposed by the number of valences produced in each synthon. A synthon must have at least one available valence, but may have more. The synthetic complexity of dealing with multiple valences in a synthon also raises the cost of producing further synthons. The inventors have determined that the use of 6 synthetic steps of average difficult results in a reasonable cost.

The total number of synthons that can be generated from presently available commercial reagents without great difficulty (relatively low synthetic cost) using the synthon generator of the present invention is approximately $5 \times 10^6$ synthons. For complete molecules which would be assembled typically from three fragments (pieces), up to approximately $10^{20}$ possible three dimensional molecular structures can be searched for similarity to fragments from a query molecule. This far exceeds by at least 11 orders of magnitude the number of all known compounds (approximately $2 \times 10^8$) as reported by the ACS. The number of possible synthons is even greater if previously generated synthons are used (bimolecular reactions) to produce yet further synthons by applying the same type/sets of reaction mechanisms.

The process and outcomes of recursive synthon generation can perhaps best be understood through a limited example, such as that shown in FIG. 1. Phenethylamine (B), a commercially available building block, directly affords only the amino synthon (nucleophilic C). However phenethylamine can also be cyclized in various ways, for example with a phosgene equivalent to form lactam (E). Although (E) lacks an open valence and so is not itself a synthon, the recursive processing of (E) then generates a synthon, the nucleophilic (H).

The Pictet-Spengler reaction represented by B-D shows how recursive synthon generation handles the many important reactions that join two pieces by forming a new heterocyclic ring. The problem that is overcome in dealing with such cyclizations in the synthon generator is that the topomer methodology, which is to be used to search for shape similarity, requires that synthons be connected by acyclic bonds, but the new bonds formed by the laboratory reactions employed by the synthon generator are instead actually internal to the new ring. This solution to this problem is addressed within the definitions of these reactions, by representing the reaction outcome to displace those actual cyclic bond(s) to the nearest appropriate acyclic bond. Thus in the B→D example, the actual cyclic bonds formed, by the insertion of the carbon between the nitrogen and the phenyl to produce a new ring, are displaced to become the new open valence labeled "pictspeng". In the actual reaction, this inserted carbon atom is provided by an aldehyde (not shown, but having the general structure R'CH=O). So in order to complete the representation of this displacement, a complementary reaction applicable to all aldehydes is incorporated into the synthon generator that sheds that carbon (R'CH=O á R'[pictspengal]) and generates a complementary "pictspengal" open valence.

When searching the synthon data base, synthons having a "pictspeng" open valence then must always be combined with synthons bearing a "pictspengal" valence.

Another major feature of the recursive synthon generator is the production sequences of steps whose feasibility can readily be evaluated by synthetic chemists. To achieve this, further reactions of synthons that include an open valence are limited to those that generate additional open valences without introducing additional atoms. To illustrate this principle, consider the two paths within FIG. 1 that connect synthon B to synthon G. The path leading through C requires the addition of an atom to C, which already contains an open valence, and so although C is formed, the C→G step as shown will actually be suppressed. However, the path leading through D is completely acceptable, because its second D→G step involves only the removal of an atom. Of the two conceptual paths from C to G shown, the survivor is the path that most probably represents the order of synthetic steps in the laboratory, and therefore the one which will be most intelligible to the synthetic chemist.

For purposes of this patent document, when "synthons" resulting from the synthon generator are referenced, it is intended that synthons directly generated by the synthetic reaction mechanisms (such as "C") as well as synthons generated by the application of an additional reaction to multistep intermediates (such as "H") are meant to be included in the reference. The operation of the synthon generator upon commercially available reagents also results in the generation of the same synthons as were generated as "structural variations" in U.S. Pat. No. 6,240,374. These synthons are those that are contributed to a synthetic reaction sequence by each commercially available reagent. These synthons, along with all the synthons resulting from the recursive application of the synthon generator are stored in the searching database.

Shown along with the reaction definition accompanying each reaction arrow in FIG. 1 are bracketed negative numbers. As noted above, performing any particular synthetic organic chemical reaction has some cost or difficulty, and each of these numbers is an approximate estimate of the cost of that particular step on that particular structure. (Less negative represents a lower cost). Summing these numbers along a sequence of steps yields a total sequence cost. In practice, one of the major limitations on the in-principle-unbounded structural output of the recursive synthon generator is a maximum allowed cost for any individual synthon.

It is well known that due to the experience and familiarity of different chemists in different laboratories with different reactions, some reactions may be easier/simpler to accomplish in some laboratories than in others. Consequently, the cost values of the numbers for each reaction type may be varied to reflect the experience of the end user chemists. In addition, some sequences of reactions may be easier to carry out for a given initial reagent than others. This will also effect the number of recursive steps that may be followed in practice for any given reagent. It has been the experience of the inventors that, typically, an average of somewhere between 20 to 30 synthons are easily and routinely generated from each initial reagent without incurring too high a synthetic penalty cost. Of course, to obtain particularly interesting or significant synthons, one may elect to incur the higher associated cost of more synthetic steps.

a. Reaction Description

A general language has been devised for describing synthetic reactions for the recursive synthon generator of the present invention. The starting point is "Sybyl Line Notation" (SLN), Tripos's functionally rich notation for chemical structures based on the more widely known SMILES notation (Ash et al.[5]). The resulting recursive synthon generation language is readily explained by means of an example. The complete current description of a structurally very simple reaction, the conversion of an O—H into a nucleophilic synthon ("O_n") is set forth in Table I.

TABLE I

ID 2 O_n
SLN HOC
HOW MARKX,1,X1
VCLASS X1,n
COST +2
RXN_CLASS ActiveH 2
INCOMPAT N[not=N*Pr,N*Hev=Het]H
EQUIV 1 all
EQUIV_ORDER HOC(=O) HOC:Hev HOCH2Hev HOCH(Hev)Hev
    HOC(Hev)(Hev)Hev
VRXN_CLASS 2 56,57,58,59

An "ID" line begins description of a new reaction, by associating a user-understandable name "O_n" with an internal identifier "2". The "SLN" line defines the connected pattern of atoms and bonds that must be present in a structure to apply this reaction, as "HOC". The "HOW" line describes how the synthon is to be generated, by listing the individual operations to be performed on the SLN pattern. Here there is only one such operation, the conversion of a real atom into an open valence "MARKX", to be labeled "X1", with the disappearing real atom being atom "1" (the H) within the SLN pattern. The "VCLASS" line defines the chemical properties of "X1" as "n" (nucleophilic). A separate table records mutually reactive "VCLASS's", in this case reporting that "n" reacts with "e". The relative "COST" of this synthetic step is "+2" (which when added to the average step cost of −5 yields a total step cost of −3, for a relatively easy reaction).

In the laboratory, most reactions on most reactants are seriously complicated by the presence of other more reactive groups. The "RXN_CLASS" line classifies this reaction as a member of the "ActiveH" family. A separately generated list of all the SLNs which are members of the "ActiveH" family is ordered by their descending reactivities. A prospective reactant is checked for the occurrence of these SLNs in the list, traversing the list until the "SLN" defining this reaction is encountered. Any SLN thereby encountered before the SLN defining this reaction is encountered describes a more reactive "ActiveH" that will prevent the intended reaction. The "INCOMPAT" line considers the same issue in a reaction-specific manner, by listing the SLNs of groups whose presence prevents this specific reaction. In this example, any "N . . . H" whose nitrogen is not protected ("N*Pr") or is not amidic ("N*Hev=Het").

The two "EQUIV" lines provide guidance when the reactant contains multiple occurrences of "SLN". As an example in this case, consider the reactant glycerol (HOCH2CH(OH) CH$_{20}$H). The "all" keyword enables generation of the trivalent synthon "[n]-OCH2CH(O-[n])CH$_2$O-[n]", by applying the "HOW" operation to each occurrence of "HOC". The "EQUIV_ORDER" information guides the possibility of generating a monovalent synthon. Its SLN patterns are compared, left-to-right in presumed order of decreasing reactivity, with the three matches for "HOC" within glycerol, starting the comparison with atom "1". The first successful comparison is the pattern "HOCH2Hev", which indicates that the monovalent synthon "[n]-OCH2CH(OH)CH$_2$OH" could be a product from glycerol. It should be noted that in glycerol there are actually two HOCH2Hev patterns, which should prevent the monovalent synthon from being formed. However, in cases of this type, the gensyn program further recognizes that those two HOCH2Hev patterns are completely identical, hence interchangeable, and so only the monovalent synthon is specified.

Figure 2:
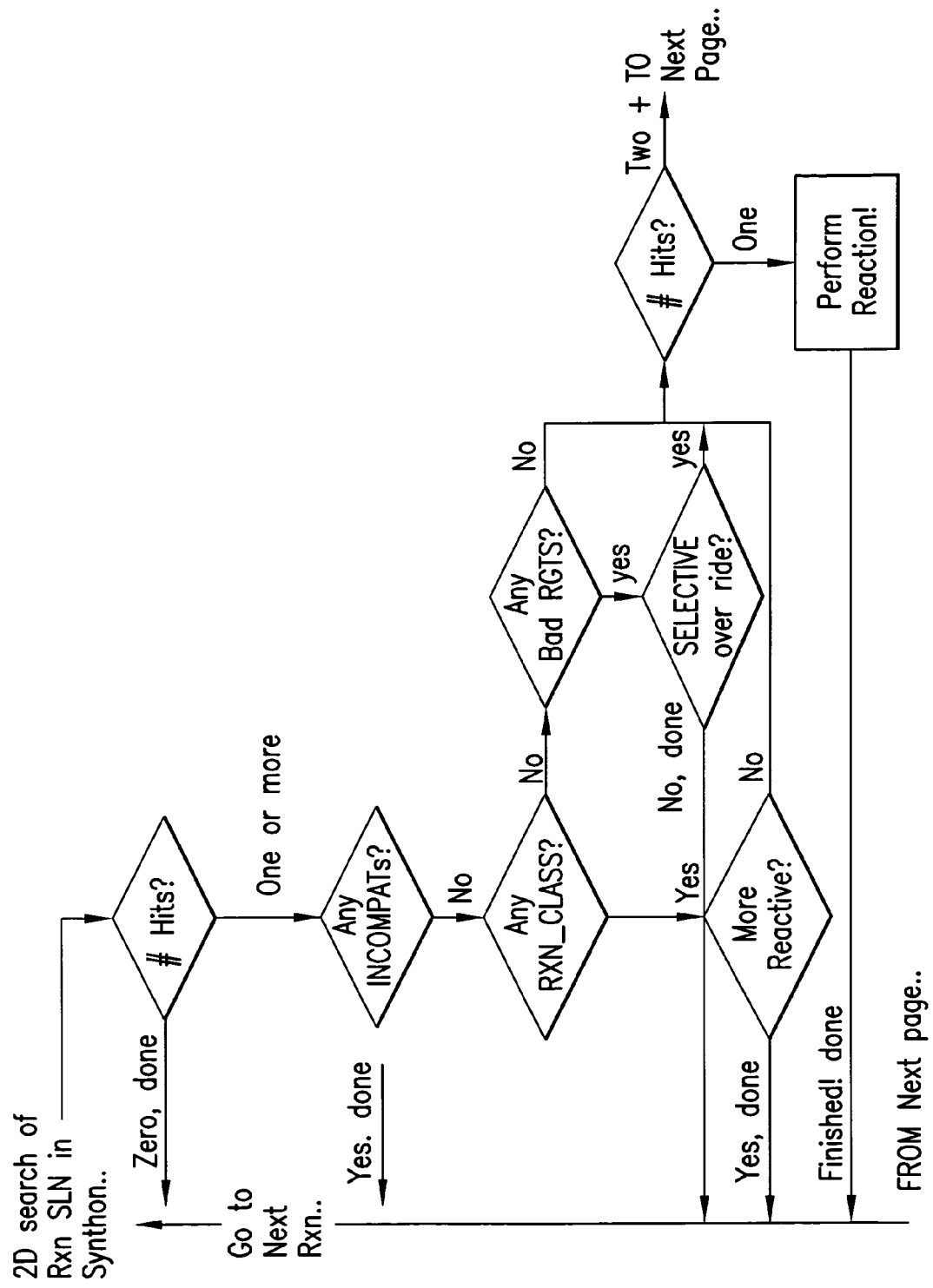
FIG. 2 illustrates the first part of the overall flow of synthon generation.
Figure 3:
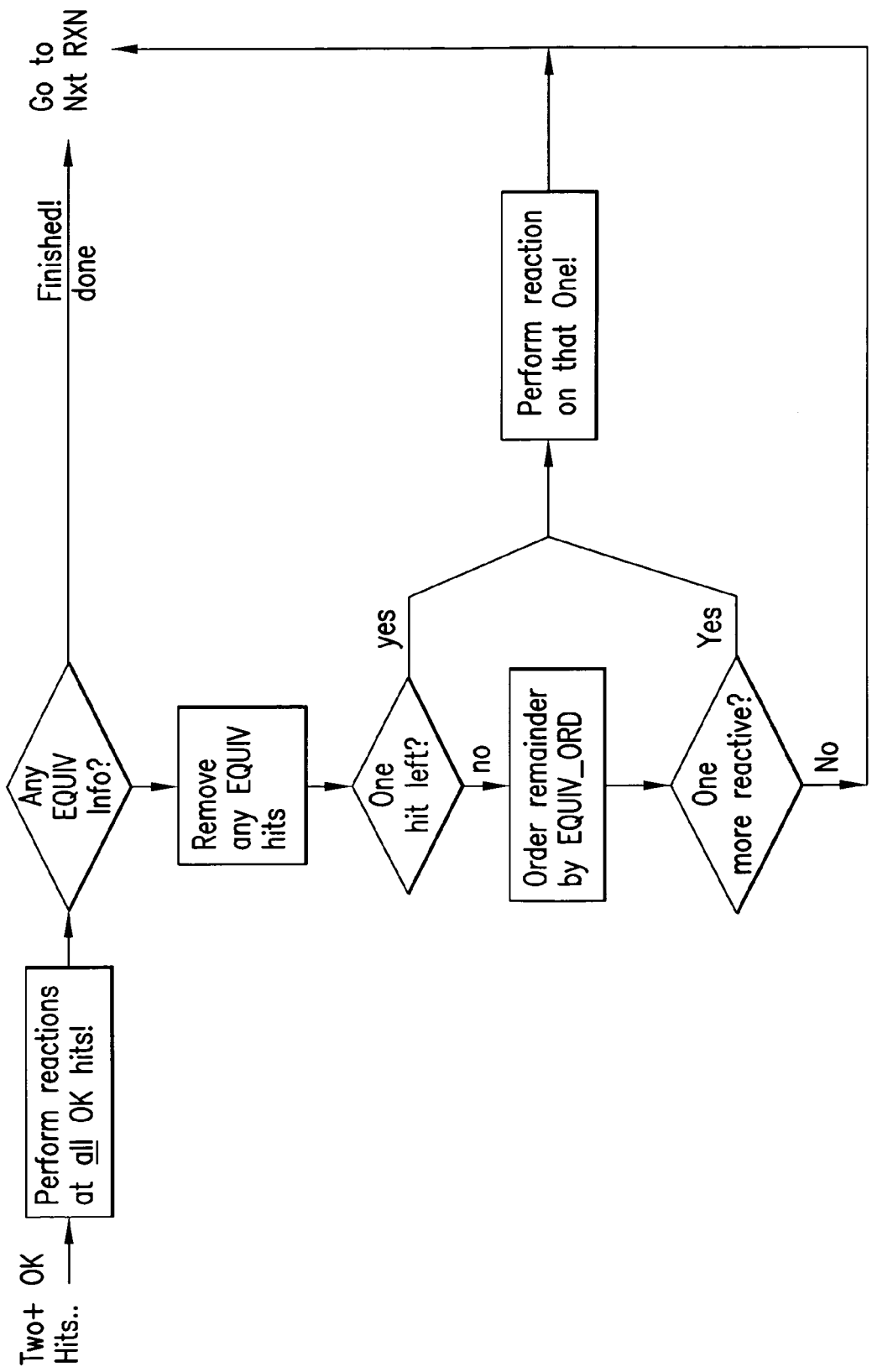
FIG. 3 illustrates the second part of the overall flow of synthon generation.
Figure 4:
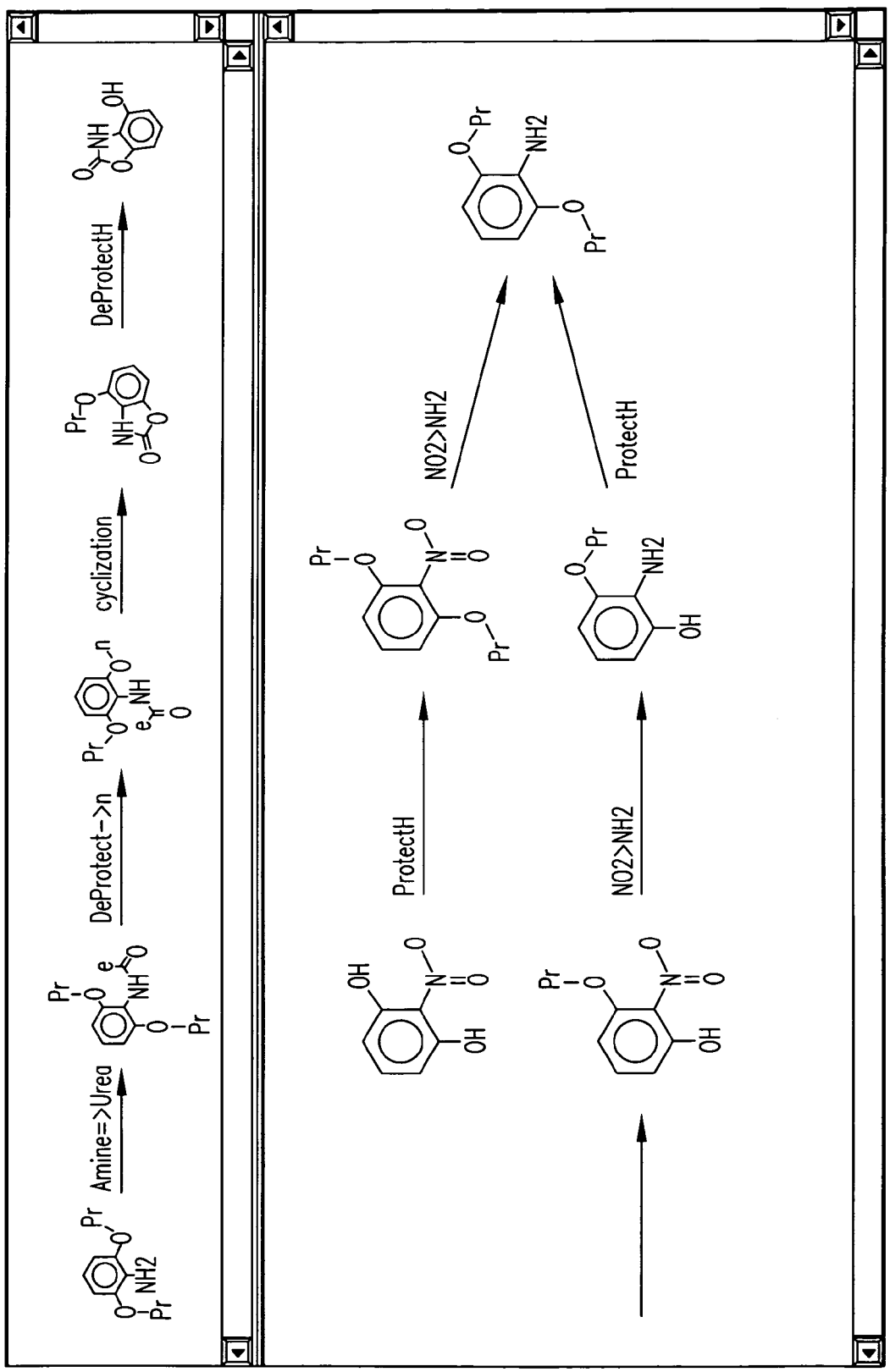
FIG. 4 shows the first part of an exemplary forward synthetic route generated by the computer-implemented method of the invention.
Figure 5:
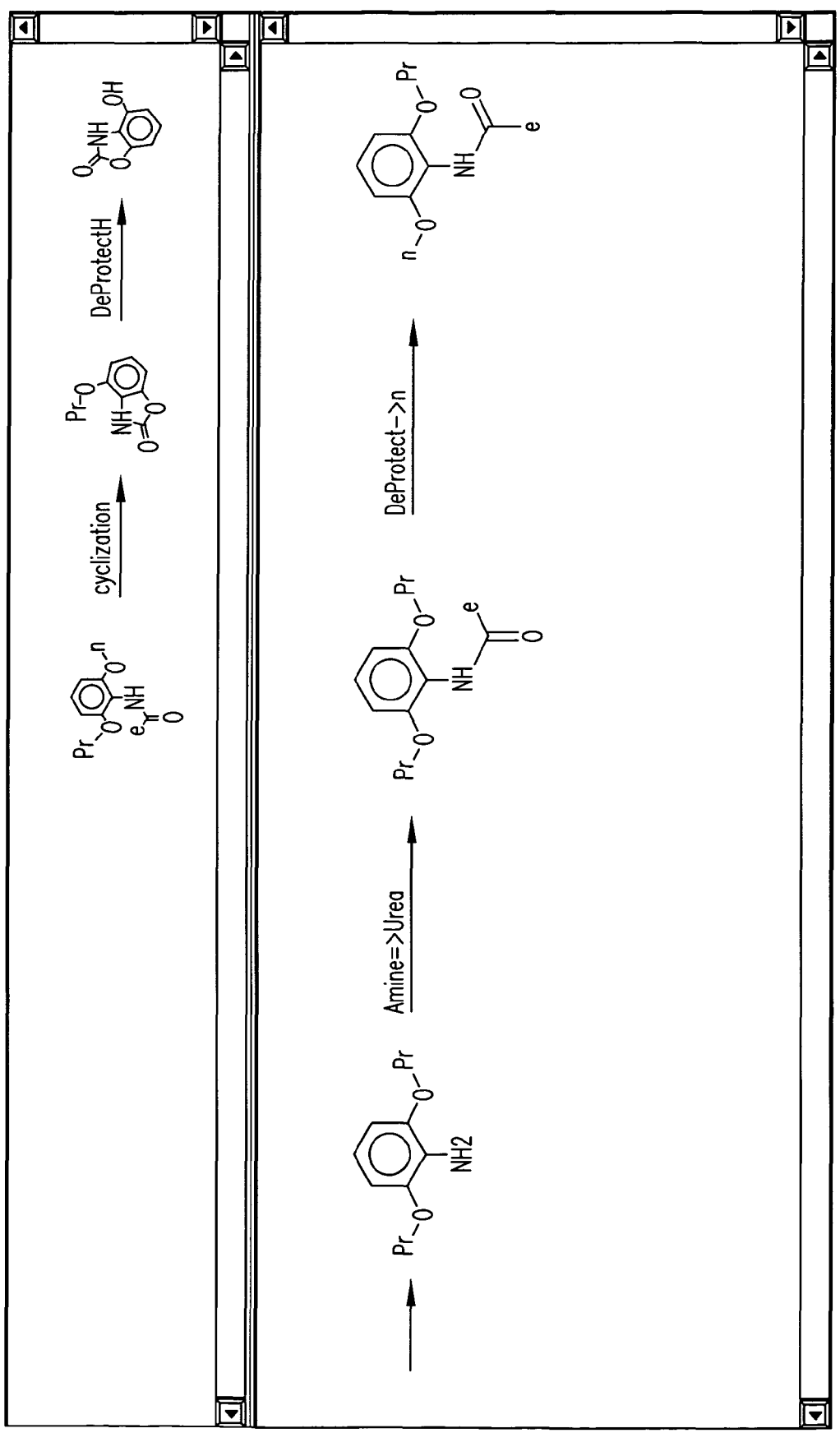
FIG. 5 shows the second part of an exemplary forward synthetic route generated by the computer-implemented method of the invention.
Figure 6:
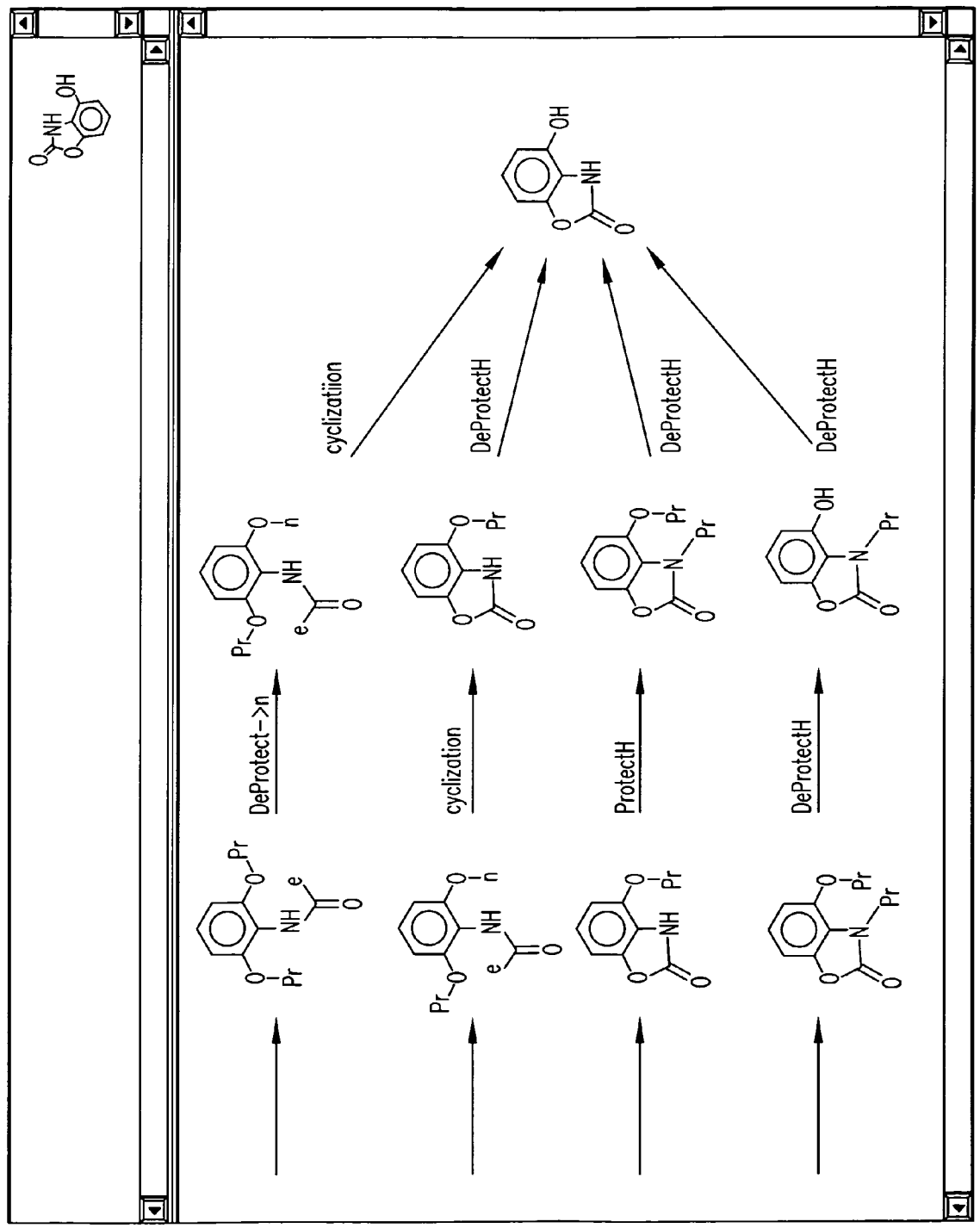
FIG. 6 shows the third part of an exemplary forward synthetic route generated by the computer-implemented method of the invention.

The "VRXN_CLASS" line links this generalized reaction description to various particular reaction subclasses, whose distinctive behavior in the practice of combinatorial chemistry is already well established. For example in the reference listing adopted by the inventors, "56" references primary alcohols, which are desirable to handle together in laboratory synthesis because of their high reactivity. The "2" references the "O" within the original "SLN". The overall flow of the recursive synthon generation method is shown in FIG. 2 and FIG. 3. An example of the application of the synthon generator is shown in the main larger panels of FIG. 4, FIG. 5, and FIG. 6. The reaction product on the far right of FIG. 4 appears as the starting point on the left for the reaction of FIG. 5. Similarly, the reaction produces of FIG. 5 appears as the starting point on the left for the reaction of FIG. 6. In both FIG. 4 and FIG. 6 alternative possible routes to the same end product are shown. The alternative routes are stored in the searching data base along with the synthon definition. In the final output, it frequently occurs that many identical synthon structures will be shown as being similar to a given query fragment. Each of the identical synthon structures corresponds to an alternative synthetic route which is available to synthesize that structure. In this way, the chemist user is provided with a possible variety of chemistries with which to synthesize a given synthon. In addition, if a synthon with an identical structure to another synthon is identified that has a different reactivity for the same open valence, the method of this invention supports such occurrences and the software code provided in the program listing appendix recognize this situation. The top panel in the Figures shows the overall synthetic flow. Reaction pathways as shown in FIGS. 4, 5, and 6 as well as other information about the synthons that is stored as output in the data base by the synthon generator is viewed by the chemist user using the display program provided in the software appendix as synth_dialog.py and synth_tree.py. The chemist user can also use the viewer in other ways such as to view examples of the way in which particular reactions were employed by the synthon generator to better understand the scope and limitations of reaction applicability. In addition, the synthon generator output contained in the Oracle data base may be searched and viewed in as many different ways as permitted by standard well known or specially created relational data base retrieval methods.

All current reaction descriptions may be found in the "sln2synthon.dat" file accompanying this application. The currently supporting information for the VCLASS, RXN_CLASS, and VRXN_CLASS keywords appear in other associated files. In practice the contents of these files are read into Oracle tables. These reaction descriptions are necessarily dynamic, if only because our understanding of the scope of reactions develops. As the underlying reaction descriptions evolve it is necessary to maintain the synthon library. On the attached CD-ROM is a complete listing of the reactions presently coded into the synthon generator. Based upon the description above, those skilled in the art will be able to add additional reactions which they may employ.

Each synthon is associated with a particular type of reactivity dependent upon the nature of its synthesis. A description of each synthon, along with information on the synthetic route to its creation and the associated costs is stored in a relational data base. Additional information related to each synthon, including but not limited to reaction conditions or the commercial source of the starting reagents, may also be stored in the data base.

Once the synthons have been generated by the synthon generator, they are topmerically aligned and their steric fields calculated. The filed data is stored along with the synthon definition and any other desired information including, but not limited to, such information as synthetic route, availability of starting reagents, and synthetic costs (as described above).

D. Generation and Metric Characterization of Synthons and Fragments

1. Query Fragmentation

As noted above, the ultimate goal of topomeric searching is to identify, using a validated molecular structural descriptor, those synthons whose overall three dimensional shape and likely biological activity is similar to fragments obtained from a query molecule that is known to possess a desired biological property. Accordingly, the query molecule must be fragmented in a manner which generates fragments possessing at least one open valence in order to have the fragment shapes compared to the synthons. Generally, the query molecule will not have resulted from a combinatorial synthesis, and, in fact, no knowledge of a possible synthetic route to the query molecule may be available. A particular difficulty is that a query molecule can be fragmented in very many ways.

Based upon their experience with fragmenting molecules, the inventors have determined that for medicinal type molecules the following fragmentation rule produces meaningful fragments:

"Break the molecule at acyclic bonds either singly or in pairs to generate sets of either 2 or 3 fragments respectively where each fragment must contain greater than a user specified number of heavy atoms."

Figure 7:
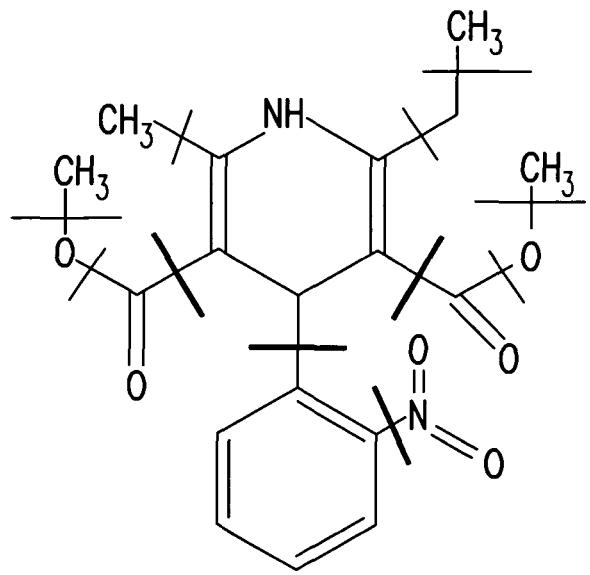
FIG. 7 shows an example of a two piece fragmentation.

For example, assuming a setting that every fragment must contain at least three heavy atoms, FIG. 7 shows an example of how the rule is applied in a typical molecule to generate fragments. To generate the fragments, the whole structure is evaluated for each new fragmentation position. The two-piece fragmentations which will be performed are indicted by the thick lines. The two-piece fragmentations that will not be performed (because one of the resulting fragments contains less than three heavy atoms) are indicated by the thin lines. In this example, if, instead of requiring three heavy atoms, the user required five heavy atoms, then only the fragmentation between the two rings would be performed.

Figure 8:
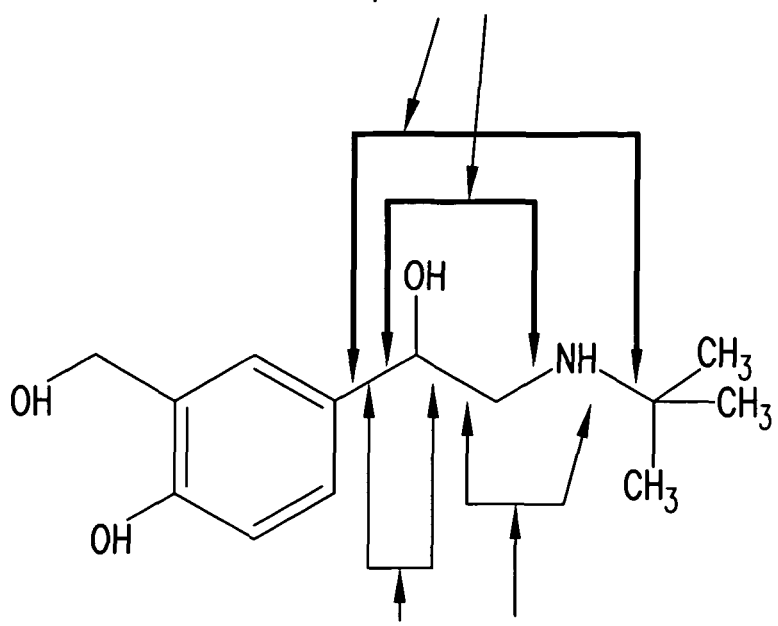
FIG. 8 shows an example of a three piece fragmentation.

An example of a three piece fragmentation is shown in FIG. 8. Assuming again a setting that every fragment must contain at least three heavy atoms, the heavy lines indicate by arrows the two positions in which the molecule would be fragmented into 3 fragments. The light lines indicate by arrows some of the three piece fragmentations that will not be performed because at least one of the fragments has fewer than three heavy atoms. If, instead of requiring three heavy atoms, the user required five heavy atoms, then no three-piece fragmentations would be performed.

Fragmenting produces most useful results when the break is next to a ring. The inventors have also noted that, because most synthons generated by the synthon generator are relatively large, a cut off using four heavy atoms is advantageous. At the present time, it has been found that generating three fragments is necessary when a two fragment scheme does not yield significant results, that is, yields relatively few shape matches. The three fragment scheme seems to find similar shapes that are sometimes missed in two fragment analysis. However, due to the higher computational overhead of three fragment searching, searches are first performed at the two fragment level. Four or more fragment searches may be necessary for some types of molecules such as the large molecule fragmentation discussed below. The searching method of the present invention described later is not limited to the number of fragments which are generated but is generally applicable to as many fragments as the user wishes to consider.

Figure 9C:
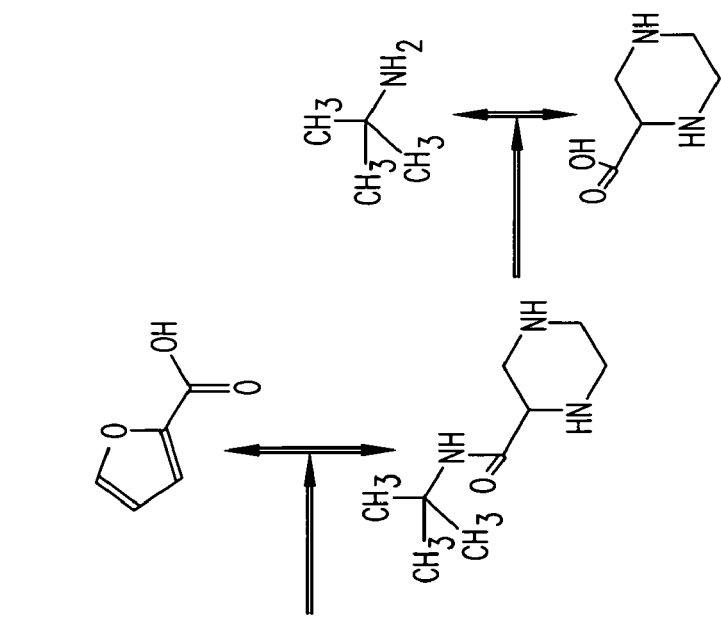
FIG. 9 illustrates fragmentation of a complex medicinal type molecule.
Figure 9B:
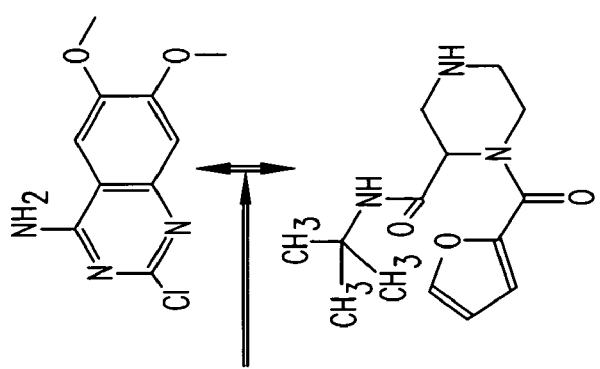
Figure 9A:
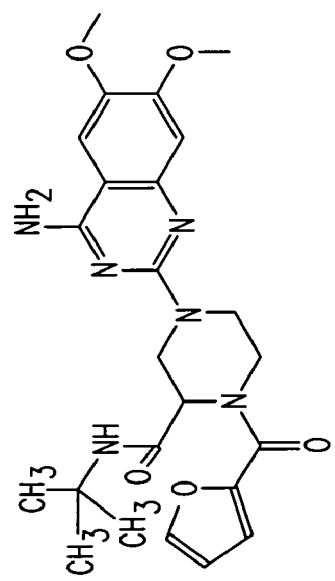

Most medicinal type of molecules will have several acyclic bonds and can be cut into several fragments. A typical fragmentation that a complex molecule would undergo utilizing the rule set out above is shown in FIG. 9. An initial fragmentation of structure (A) in FIG. 9 would cut the molecule at the acyclic bond between the pteridyl group and the rest of the molecule. A subsequent cut of structure (B) at the acyclic bond would remove the 2-furanoyl group leaving the remaining 2-carboxylpiperazine, structure (C). A third acyclic bond cut would produce the t-butylamine fragment and the piperazine fragment. At each stage the resulting fragments could be topomerically aligned and their steric fields calculated for comparison to available synthons. Alternatively, for complex molecules, the approach to fragmentation using fragmentation tables as set out in U.S. Pat. No. 6,240,374 may be employed.

2. Generation of Topomer Alignment for both Synthons and Query Fragments

The following is the best mode for topomeric alignment currently known to the inventors. The stepwise procedure for generating the topomer of a monovalent molecular synthon or fragment may be very briefly summarized as follows:

1) A structurally distinctive "cap" is attached to the open valence, and a Concord™ or similar three-dimensional model is generated for the resulting complete structure;

2) This model is oriented to superimpose the "cap" attachment bond ("root") onto a vector fixed in Cartesian space;

3) Proceeding away from this "root" attachment bond, only as required to place the "most important" (typically the largest) unprocessed group farthest from the root and the next most important to the "right" of the largest (when looking away from the root along the current bond), acyclic torsional angles may be adjusted, "stereocenters" inverted[6], and ring "puckerings" standardized; and 4) Removal of the cap completes the topomer conformation.

Note that the conventional force field energy (intramolecular enthalpy) of a topomer is altogether immaterial. For example any steric clashes that may result from topomer generation are completely ignored The first, second, and fourth steps are routine and easily accomplished by those skilled in the art. The third step in the topomer generation procedure is unique and is set forth in detail as follows. The following description is "bottom-up", beginning with more precise definitions of the various structural elements that may need adjustment (torsions, (pro) chiralities, "puckerings") and the natures of those adjustments. "Precedence" rules for ordering a set of attached groups (to any atom of interest) are also set forth. The entire topomer generation procedure is then described, supported by a structural example.

a. Bond Torsions

During topomer generation, the "torsion" or dihedral angle of almost every acyclic skeletal bond is measured and usually altered. This operation requires the identification of four consecutively connected atoms, i.e., the two atoms that define the bond, plus a selected atom attached to each of those defining atoms. This assembly will be referenced below as a-b-c-d, with b always designating the end of the bond that is topologically nearer the "root". Precedence rules to be presented below determine which of the candidate atoms, attached to b or c, become designated as a and d. The final setting of an a-b-c-d dihedral angle depends on whether the a-b and c-d bonds are cyclic or not (b-c of course is acyclic). If both are acyclic (or if b-c is an amide or multiple bond), a-b-c-d becomes 180 degrees; if neither is acyclic, a-b-c-d becomes 60 degrees; if only one is acyclic, a-b-c-d becomes 90 degrees.

b. (Pro)Chirality

The atoms whose attachments require assessment for left/right(ness) are a superset of those that are formally chiral within 3D molecular models. Not only must pyramidal $sp^3$ nitrogen be included, but also enantiotopic[7] atoms. For example, an isopropyl group (—CH(CH$_3$)CH$_3$), after one of the methyl groups is designated as having highest precedence, the remaining ?H and ?CH$_3$ groups become non-equivalent. Furthermore and in contrast to torsions, chiral atoms within rings are also inspected and adjusted whenever both attachment bonds are acyclic.

The left/right(ness) of a particular attachment proved easy to assess on the computer screen but surprisingly difficult to determine computationally. Note that the objective is control of "local" left/right(ness), relative to the other atoms being processed concurrently, not "global" left/right(ness). For example, if the overall fragment were a phenyl with a complex ortho substituent, local "right(ness)" within the ortho substituent will be "left(ness)" within the global coordinate system. Searches for congruent algorithms within the prior art computer graphics and interactive gaming literature which might be used yielded no results. Accordingly, the following heuristic was empirically derived and does correctly perceive the geometry.

The geometric objective is to determine whether or not a fourth point a4 is to the "right" of a plane a1-a2-a3, where the a1-a2-a3 order also establishes the viewing direction (along a1=>a3). The first test is whether the a1-a2-a3 plane is parallel to any of the three global coordinate planes (e.g., perpendicular to any of the three Cartesian axes), which in practice means that none of the individual a1, a2, or a3 x-, y-, or z-coordinate values differs from their mean by more than 0.2 A. If so, then determining the left(right)ness of a4 requires only the comparison of the appropriate a4 coordinate value to the mean coordinate value, while considering the viewing direction.

If the a1-a2-a3 plane is not parallel to a global coordinate plane, then the cross-product of a1=>a2 (becoming v1) and a2=>a3 (becoming v2) is formed, as usual except that if any of the values of a1=>a2 or a2=>a3 are within 0.1 of 0.0, they become exactly 0.0. The vector a2=>a4 (if the atom a4 is bonded to a2) or a3=>a4 (if a4 is bonded to a3) is also formed (with the same rounding of values <0.1 to 0.0), to become v3. The remaining steps depend on which of the three elements of the cross-product v3 has the largest magnitude. If the first element is largest, then a4 is on the right of the plane (or on the left if v1.z times v3.x is greater than 0). If the second element is largest, then a4 is on the right if v1.x times v3.y is less than 0. Finally, if the magnitude of the third cross-product element is largest, then a4 is on the right if v1.x times v3.z is greater than 0.

To correct any attachment a4 that is thus found to be on the wrong (left) side of the plane, all atoms in all groups that are attached to the atom to which a4 is attached are reflected through that a1-a2-a3 plane.

c. Puckering

Ring systems that have some degree of non-planarity can, much like chiral atoms, exist in either of two geometric forms having equivalent internal strain energy (though non-bonded interactions with atoms external to that ring system are usually not equivalent). For example, consider the reflection of a chair conformation of the (possibly substituted) cyclohexyl fragment through the plane formed by its 1, 2, and 6 carbon atoms to create an alternate chair form. To obtain an invariant geometry for such fragments, the puckering must be standardized in much the same way that (pro)chirality is standardized, as follows. Whenever the topomer generation process encounters the first bond within a new ring system, an "entry plane" is generated from the two atoms at the end of that first cyclic bond and the last atom in the encountering chain. Then the entire ring system is enumerated (by growing the largest tree that can be grown from that ring bond without including any acyclic bonds). Two summary scores for the ring system are determined, a non-planarity (sum of the Angstrom distances of those ring atoms from the entry plane), and a non-planarity-weighted centroid (sums of x, y, and z coordinates over all ring atoms, but with each coordinate multiplied by the distance of that ring atom from the entry plane, divided by the non-planarity score). The ring system is considered planar and no action is taken if its non-planarity score is less than 0.5. Otherwise the dihedral angle is calculated between the entry plane and a second plane defined by the same two initial ring atoms and the non-planarity-weighted centroid. If this angle is less than 180 degrees no action need be taken. Otherwise all the atoms in the ring system, this time including all its attachments except the entry attachment, are reflected through the entry plane.

d. Precedence Rules

These rules determine which, among a set of attachments to an atom of interest, the torsional and (pro)chiral operations are to affect. The precedence of an attachment is mostly determined by the relative properties of its "path", so the first step in establishing the relative precedence among a set of attachments is to enumerate their paths. Whenever the attachment bond is acyclic, its path will simply include all the atoms in the implicit "side chain". However, whenever the attachment bond is cyclic, its path is defined to consist only of those atoms with a "topological distance" (number of separating bonds) to the attachment point that is less than any alternative topological distance back to the starting point. To take as an example the (possibly substituted) phenyl side chain, with the two "attachment" atoms to consider being its 2 and 6 carbons, the path generated by the 2 carbon will include the 2 and 3 carbons plus their attachments, and the path generated by the 6 carbon will include the 5 and 6 carbons plus their attachments, but the 4 carbon plus its attachment (being topologically equidistant by both paths to the starting point) will belong to neither path. A more complicated example is the 2-naphthyl side chain. The path originating from the 3 carbon will include only the 3 and 4 carbons and their attachments. The other path from the 1 carbon will include all the other naphthyl carbons and their attachments, excepting only the fusion carbon between the 4 and 5 carbons that is equidistant from the starting point.

There is one other major determinant of attachment precedence. The overall topomer generation process usually imposes an additional distinction, between those attachment atom(s) whose path(s) include the root atom of the topomer and those whose paths do not. Depending on the current step in topomer generation, such "rooted attachments" will either be completely suppressed or else given the highest precedence. In the latter case, each individual path ends whenever the root atom is encountered, and the highest precedent attachment will be the one whose topological distance to that root is shortest.

Once such paths have been generated for each of the candidate attachments, the precedence order of those attachments is determined. This process applies an ordered set of rules in a strictly hierarchical fashion, such that lower rules are applied only to break ties that remain after the application of higher rules. In order of application, these rules are:

1) only when a root atom is specified, the path whose topological distance to that root atom is shortest has precedence;
2) the path containing the largest number of atoms has precedence;
3) the path having the largest molecular weight (sum of atomic weights) has precedence;
4) the path having the highest sum of atomic weights, each atomic weight being divided by its topological distance to the root atom, has precedence (thus within 2,5-dimethylphenyl the path rooted at atom 2 has precedence over that rooted at atom 6);
5) only when a root atom is specified, an ambiguity can remain that the following rule addresses. First an illustrative example. Assume the fragment is 4-methoxyphenyl, requiring an adjustment of the torsion of the phenyloxygen bond, and thereby the position of the methoxy methyl. The 3- and the 5-carbons have equal precedence according to rules 1-4, so either could become atom a (recalling the a-b-c-d nomenclature to define a torsion), thereby producing two very different possible locations for the methyl (and especially for any attachments to the methyl group). To resolve this ambiguity, the path whose attachment atom is to the local right (determined as described above) of the plane defined by the root atom and the b-c atoms is assigned the higher precedence. (If the root atom and the b-c atoms are collinear, as indeed in the example, and so can not define a plane, then the x-y plane is used instead.)

e. General Procedure for Topomer Generation

The overall geometry adjustment process, the third step in topomer generation, can now be described, referring as necessary to the above descriptions of individual entities. This procedure is applied to all synthons and all fragments to obtain the topomer alignment for each. The first step is to construct a "(pro)chiral list" of all tetrahedral acyclic atoms attached to at most one hydrogen. This (pro)chiral list is combined with a list of all atoms that are non-terminal, and that are the end-point of an acyclic and non-triple "qualifying" bond, and that also are topologically nearer the root than the alternative end-point of that bond. This "qualifying bond list" also includes the temporary bond from the root atom to the temporary cap fragment, because the setting of its torsion fixes the third degree of freedom in the overall orientation of the topomer. Also the attaching atom within the cap is added to the list of "current atoms". This "current atom" list is ordered by increasing topological distance to the attaching atom within the cap and processed in that atom-by-atom order, as follows:

1) If the current atom is included on the (pro)chiral list, perform the (pro)chirality operation on its attachments (with paths to the root atom being omitted from its precedence candidates).

2) On each of the current bonds between the current atom and an attachment farther from the root, perform the torsional operation as follows. No action if the bond is not a "qualified bond", otherwise the a atom will be the highest in precedence among the current atom attachments, specifically the shortest atom path to the root (no action being taken if this a-b bond is triple). The d atom will be the highest in precedence among the attachments to b, of course excluding a itself.

3) For each such torsional operation, only if the c-d bond is cyclic. Ensure that d is indeed local right of the a-b-c plane, and if not, reset the a-b-c-d torsion to 180 degrees greater than its current value. (Some bonds between non-planar rings will require this additional action.) Then perform the pucker operation with respect to the c-d bond (the "entry plane" being b-c-d).

Completely processing the "current atom list" in this fashion yields the final topomer conformation.

f. Example Alignment Process

Figure 10:
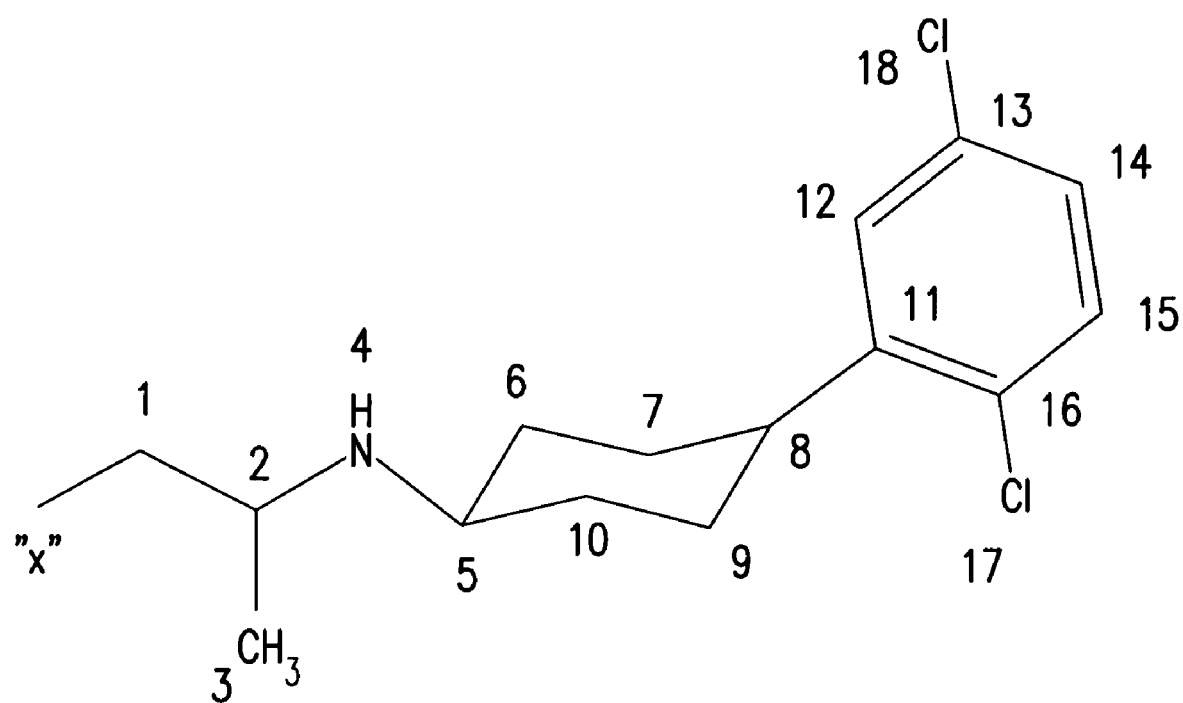
FIG. 10 illustrates a representative fragment labeled to identify the atoms which undergo a topomeric alignment.

To further illustrate the process of topomer generation, the topomeric alignment of the fragment example in FIG. 10 will be described. The cap is on the left, the cap attaching atom being atom "1" and the remainder of the cap being denoted by "x". (Thus the input structure and the final topomer after removal of the cap do not include atom "1".) Hydrogens that do not affect the resulting topomer conformation are omitted for clarity. It may be seen that the (pro)chiral list (all tetrahedral acyclic atoms attached to at most one hydrogen) contains atoms 2 and 4. The acyclic bonds between atoms 1-2, 2-3, 2-4, 4-5, and 8-11 become the "qualified bond" list, so the final list of "current atoms" to be traversed during topomer generation is 1, 2, 4, and 8. Proceeding in order down this list:

Atom 1: No (pro)chirality operation is needed since atom 1 is not on the (pro)chiral list. The 1-2 bond needs its torsional angle set, and so the precedence of the attachments to the 1-2 bonds must be established. The first precedence rule "take the path to the root" establishes the position designated by "x"_as the a atom (within the a-b-c-d specification), while the next precedence rule "take the attachment with the most atoms" clearly favors atom 4 over atom 3 as the d atom. Therefore the dihedral angle of the x-1-2-4 bond is changed to 180 degrees, to appear much as shown. The 2-4 bond is not in a ring so no pucker adjustment need be considered.

Atom 2: Its highest precedent attachment (excluding the root) is again the remainder of the fragment. However atom 2 is on the (pro)chiral list, so the (pro)chirality standardization procedure described above is applied to atom 2. There are then two bonds away from atom 2 whose torsions need attention, 2-3 and 2-4. In both cases atom 1 as the head of the shortest path to the root becomes the a atom. All of the attachments to atom 3 (hydrogens) are equivalent in precedence, so the selection of the d atom is completely arbitrary, the topomer geometry of course becoming the same regardless of which hydrogen becomes the d atom in the setting of 1-2-3-H to 180 degrees. Finally the dihedral angle about 2-4 can be addressed. There are two attachments to atom 4, the hydrogen and the rest of the fragment, the latter having higher precedence because it has more atoms so that it is the 1-2-4-5 dihedral which is set to 180 degrees.

Atom 4: Its highest precedent attachment (excluding the root) is again the remainder of the fragment. There is only one other attachment to 4, the hydrogen as shown. Since 4 is found in the (pro)chiral list, it must be adjusted as described above (to ensure that the hydrogen is located to the right of the main chain). There is one torsional angle to be established. Its a atom is again determined by the shortest path back to the route. However the selection of the d atom is complicated. It will be evident that the paths away from atom 5, beginning with atoms 6 and 10, are topologically identical. (As noted earlier, path generation stops when another path is encountered, any overlapping atom(s) being discarded. In this case atom 8 ends both paths and so it and its attached atoms appear in neither.) However the paths are not geometrically equivalent, in that a rotation about 2-4-5-6 will yield a geometry different from the equivalent rotation about 2-4-5-10. Therefore it is the last of the precedence rules outlined earlier that yields an unambiguous geometry, selecting 6 as the candidate that is locally to the right of the 2-4-5 plane (assuming atom 6 to be closer to the viewer than atom 10). The 2-4-5-6 dihedral value will thus be the one altered; however, because the 5-6 bond is in a ring, this value is adjusted to 90 degrees, not 180 degrees.

The other consequence of the 5-6 bond being in a ring is that the pucker state of that ring must be standardized. The ring system is found to include atoms 5 through 10 (since the 8-11 bond is not in a ring, the phenyl group is not part of this ring system). The ring pucker adjustment method will indicate that atoms 5 through 10 do not lie in the 4-5-10 plane, and so the dihedral angle 1-5-10-(non-planarity-weighted-centroid of this ring system) is evaluated. If this value is greater than 180 degrees, the coordinates of all the remaining atoms 5 through 18 are reflected through the 4-5-10 plane.

Atom 8: Atom 8 is not on the (pro)chiral list. To establish the dihedral angle about bond 8-11, the precedence rules must choose between atoms 7 and 9 as the a atom and between atoms 12 and 16 as the d atom. Because the paths leading from the 7 and 9 atoms are topologically identical, the final precedence rule will be invoked, determining that it is atom 7 that is on the right of the 1-8-11 plane and so becomes a. The paths leading away from atoms 12 and 16 have the same numbers of atoms and the same molecular weights. However the sums of the atomic weights divided by the bond separations will not be equal (as a consequence of their topological difference), and so atom 16 will have higher precedence and become the d atom of the dihedral angle. The complete dihedral angle to be set is 7-8-11-16, and the value that its dihedral will take is 60 degrees, since both the 7-8 and 11-16 bonds are contained within rings.

Because the 11-16 bond is contained within a ring, the ring system including atoms 11 through 16 will be evaluated, found to be planar, and thereby require no pucker adjustment for standardization.

3. Steric Field Generation of Topomerically Aligned Synthons and Query Fragments The steric fields about a synthon or query fragment are characterized in almost exactly the same manner as that first taught in U.S. Pat. No. 5,025,388 for practicing CoMFA. In similar fashion to standard CoMFA, the fields of the topomerically aligned synthons and fragments are generated using an $sp^3$ carbon atom as the probe for the steric fields. Both the lattice spacing and the size of the overall lattice space for which data points are calculated will depend on the size of the synthon or fragment and the resolution desired. A variation on grid sizing is discussed below. The steric fields are set at a cutoff value (maximum value) as in CoMFA for lattice points whose total steric interaction with any synthon or fragment atoms is greater than the cutoff value.

One difference from the standard CoMFA field generation procedure as taught in U.S. Pat. No. 5,025,388 is that atoms which are separated from any template-matching atom by one or more rotatable bonds are set to make reduced contributions to the overall steric fields. An attenuation factor [$1^{(\text{"small number"})}$], preferably about 0.85, is applied to the steric contributions which result from these atoms. For atoms at the end of a long synthon or fragment, the attenuation factor produces very small field contributions (ie: $[0.85]^N$) where N is the number of rotatable bonds between the specified atom and the alignment template atom. This attenuation factor is applied in recognition of the fact that the rotation of the atoms provides for a flexibility of the synthon or fragment which permits the parts of the synthon or fragment furthest away from the point of attachment to assume whatever orientation may be imposed by the unknown receptor. If such atoms were weighted equally with the more anchored atoms, the contributions to the fields of the significant steric differences due to the more anchored atoms (whose disposition in the volume defined by the receptor site is most critical) would be overshadowed by the effects of these flexible atoms.

For computational convenience, one further variation of the calculated steric fields is employed to reduce the size of the fields that must be stored. The calculated steric interaction values, which are all positive, associated with each lattice point are binned into 1 of 15 levels. A 16th level is used to indicated the absence of any steric interaction value. It should be noted that the standard non-binned CoMFA steric fields could just as well be used in the methodology of the present invention. However, as mentioned above, for computational convenience binned steric CoMFA fields have been utilized.

4. Incorporation of Features

To further improve the ability of topomer searching to identify similarly shaped synthons which may be substituted for query fragments, ideas from pharmacophore modeling have been implemented for characterizing synthons and query fragments. It is well recognized that certain characteristic interactions of molecules in addition to shape play an important role in determining whether a molecule will bind to a larger biomolecule. Complimentarity of shape permits the molecules to approach each other closely enough for these interactions to take place. In pharmacophore modeling the presence and location of "feature" classes containing molecular characteristics thought important to the binding of the molecule are tracked as well as the distances and directions between the features. In this type of modeling, an absence of any given feature in a molecule or a different location is considered to significantly reduce the likelihood of that molecule's binding and, thus, typical pharmacophore modeling is an all or nothing proposition. Clearly, in the present methodology due to the topomeric alignment of synthons and query fragments all distance and direction attributes of features present in the synthons and query fragments are lost.

However, an alternative approach to incorporating the characteristic pharmachophore feature interactions in conjunction with the shape similarity matching described in more detail below has proven to generate an exceedingly powerful and accurate discovery methodology. The classic five feature classes are employed: positive charge, negative charge, hydrogen-bond-donating, hydrogen-bond-accepting, and aromatic. When present in either the query molecule fragment or the synthon, the features are assigned X,Y,Z point locations in the topomer alignment either centered on the relevant atom, or, in the case of aromatic rings, the centroid of the ring. Generating the topomer conformation of a synthon or query fragment not only fixes the steric shape of that synthon or fragment, but is also fixes the Cartesian coordinates of each pharmacophoric feature contained within the synthon or fragment.

Once the synthons have been generated by the synthon generator, they are topmerically aligned, their steric fields calculated, and the presence and location of any topomerically aligned features recorded. All this data is stored along with the synthon definition and any other desired information including, but not limited to, such information as synthetic route, availability of starting reagents, and synthetic costs (as described above) in a relational data base.

E. Molecular Comparisons

1. Topomer Similarity

The topomer similarity between a query fragment and a synthon is defined as the "distance" represented by the difference between the molecular fields which serve to characterize the query fragment and synthon shapes. As an example, take a query fragment A and a synthon B which have each been placed in their topomeric alignment and the steric field values calculated for each point in the surrounding three dimensional grids. Let each grid point be denoted by its corresponding cartesian X, Y, Z coordinate so that the grid points are defined as $X_0, Y_0, Z_0 \ldots X_N, Y_N, Z_N$. For query fragment A and synthon B the field values, $V^A$ and $V^B$, at each point in the grid are denoted as:

$$V^A_{X0,Y0,Z0} \cdots V^A_{XN,YN,ZN} \text{ and } V^B_{X0,Y0,Z0} \cdots V^B_{XN,YN,ZN}.$$

The root sum square of distances between the fields is then defined as:

$$\sqrt{(V^A_{X0,Y0,Z0}-V^B_{X0,Y0,Z0})^2+\ldots(V^A_{XN,YN,ZN}-V^B_{XN,YN,ZN})^2}$$

This distance is conveniently denoted as:

$$\sqrt{(A:B)^2}$$

For identical molecular structures, the distance equals 0. Therefore, the closer the value of the distance is to zero, the closer in shape the query fragment and the synthon will be. When searching among many possible structures, the minimum calculated value of the distance is sought. When speaking about topomer distances, a dissimilarity concept is used. Thus, the larger the distance, the more dissimilar the shapes are. A completely general distinction of all topomer dissimilarities is their method of combination. Analogously to Euclidean distances between vectors, topomeric dissimilarities combine in geometric fashion, instead of the more intuitive arithmetic fashion. Thus two dissimilarity values X and Y yield a combined dissimilarity value of $(X^2+Y^2)^{1/2}$ rather than X+Y.

2. Feature Matching

A feature search strategy can be summarized as finding all the synthons which have features, similarly located in topomer space and similar in any other detailed feature property, that match each of the features in the topomerized fragments of the query structure. In keeping with the distance definitions used for steric shape similarity, differences in features are defined with the same dimensionality as shape so that both shape and features can be used to characterize a synthon or query fragment for searching. Feature by feature differences are also combined along with shape differences in a root sum square rather than a straight sum fashion.

$$\sqrt{(A:B)_{shape}^2+(A:B)_{features}^2}$$

Thus, a second feature mismatch would not be as costly as the first one. To determine the feature "distance", each of the pharmacophoric features in the query structure fragment is considered in turn, by identifying the closest feature of the same pharmacophoric class in the synthon. If there is no such feature or if the nearest such feature is more than 1.5 Å distant, the dissimilarity sum of squares is increased by a maximum of 100×100 units. (Units are chosen to be commensurate with the steric shape units of kcal/mole-Angstrom.) If there is a matching feature within 0.5 Å, the dissimilarity is set to zero. For a feature separation between 0.5 Å and 1.5 Å the dissimilarity penalty increment is obtained by linear interpolation between 0 and 100×100 unit values. Further, it is possible to scale/weight the feature contribution to increase or decrease its relative contribution with respect to the steric contribution to the observed similarity (distance). Note that the use of the term "distance" with the feature searching methodology of the present invention is not meant to refer to an actual physical "distance" as considered in traditional pharmacophore techniques.

While the relative weight of each feature's contribution to the field can be varied, in the basic method, an attempt is made to match all features in a query with the nearest feature of the same class in the database molecule. This is similar to a pharmacophore type match, but there is no concern with matching interfeature distances in the topomeric conformation. Further, unlike standard pharmacophore searching, the user is able to assign adjustable penalties in the event that an exact match is not possible. For instance, a nearby spatial match of one type of feature might be more acceptable to the user than a nearby spatial match of another feature. The distance penalty for the spatially mismatched first feature could be set much lower than for a spatially mismatched of the second feature. The features method also permits handling of situations where a feature is present in a synthon but not in the query molecule fragment. In standard pharmacophore technique, this situation would lead to a total mismatch. However, in the present method the user can assign a distance (similarity) penalty for the absence of the match to the query, but need not totally ignore either the overall shape of the query or the contribution of the other features in judging the similarity of the structures.

3. Partial Feature Matching

It is recognized that very frequently the binding of small molecules to receptors is highly dependant on the interaction between hydrogen-bond-donating and hydrogen-bond-accepting atoms. For partial feature matching, the search for charged groups and aromatic rings may be turned off. A large penalty (10,000 units) is applied for donors and acceptors which do not align. In addition, the number of donor or acceptor matches required can be varied. This capability is included since it is recognized that frequently only 2 or 3 groups are required to make a small molecule active. For partial feature matching, all the hydrogen-bond-donating and hydrogen-bond-accepting features are examined but only those generating the lowest 2 or 3 distances (including applicable penalties) are used.

A further variation of the partial feature matching method considers the situation where the user determines that there is only one feature which is most important to match. If that feature is present and properly located, there is no penalty, the field differences are zero and the similarity is great. The flip side of single feature matching is that if the feature does not match a very large penalty is imposed to clearly yield a large difference (greater distance and low similarity).

F. Three Dimensional Searching For Similarly Shape Molecules

As seen, the dissimilarity between a synthon and a query fragment has two contributions, steric fields and pharmacophoric features, as detailed above. To summarize, the steric component combines the differences in the CoMFA-like steric fields exerted by the topomers over the intersections in a standard 2-Angstrom spaced lattice. However, these steric fields are softer than those in CoMFA because the steric effects of individual atoms diminish with distance from the root atom, by being scaled as noted above by the number of intervening rotatable bonds. As noted earlier, the pharmacophoric feature component is based on the usual designations of aromatic, positive, negative, hydrogen-bond-accepting, hydrogen-bond-donating feature classes. Topomer feature dissimilarity combines class-specific penalty values for feature instances that are either not duplicated in kind, or are else too distant in spatial location. Furthermore feature dissimilarity is not symmetric, with the penalty for an unmatched feature in a candidate hit being much smaller than the penalty for an unmatched feature in the query.

1. Data Base

In addition to the synthons generated by the synthon generator, including those that correspond to the synthons described in U.S. Pat. No. 6,240,374, the method of this invention permits custom synthons, those whose structures and method of synthesis are not easily predicted by computer, to be utilized. The source of these synthons is the standard organic synthetic literature.

All information is stored in a relational data base that is readily accessible to the search engine of the present invention.

2. Searching Methodology

The object of three dimensional searching is to identify a molecule or molecules (or equivalently, their constituent parts) that have the closest overall three dimensional shape and location of features to the shape and features of a query molecule. To accomplish this goal, the similarity of the shape and feature location of each synthon in the searching data base to the shape and feature location of each fragment of the query molecule is computed using the topomeric distance. The synthons which are closest in shape and features to the query molecule fragments are used to determine how similar in shape and features a molecule composed of those synthons will be to the overall molecular shape and features of the query molecule.

As disclosed in U.S. Pat. No. 6,185,506 and U.S. Pat. No. 6,240,374, a Topomeric Metric neighborhood distance of not greater than 80-120 indicates likely similarity in shape and biological activity. The inventors have further noted that for larger molecular fragments (synthons or query fragments) containing many more heavy atoms, a larger metric distance of greater than 120 produces useful results. Further, since the incorporation of "features" results in a larger neighborhood distance, and since at the final stage of synthon combination two or more synthons are being combined, distances of up and greater than 240 may be employed. In addition, there are circumstances where no other fragment is found within a smaller range, so that a more distant fragment may be investigated. The users of the method of the present invention may determine the cut off value for the dissimilarity distance that they believe appropriate to the circumstances. However, the larger the dissimilarity distance used, the greater the number of hits returned and the more likely will be the dissimilarity in shape and biological activity between the synthon and the query fragment.

3. Analysis and Output of Search Results

Because the recursive synthon generator produces a very large number of synthons, shape similarity searches (between those synthons, and the molecules that may be constructed from them, and a query molecule, and molecular fragments derived from the query molecule) identify an enormous number of structures for further consideration. For example, a structural query that matches only one in a trillion random structures will yield 100 million possibilities from a search of $10^{20}$ structures. Considered at the rate of a thousand structures per hour, roughly five staff-years would be needed to individually review 100 million structures.

The present inventors have devised a unique analysis and output system to handle the analysis of the data generated by a shape search using the recursively generated synthons. The information generated by the method described in this patent document may be viewed in many ways. At the present time, a visual display output system is used in which the user may look at the search data based upon the results of the similarity distance calculations. As a start, it should be recognized that the enormous number of final possible structures is simply a consequence of combinatorial assembly from much shorter lists of synthons that are shape-similar to query fragments. These lists are much easier to manipulate and view to abstract the information desired by the user.

At the start of the shape comparison process, both the query structure and the shape similarity criteria are supplied by the user. Note in particular that the user-supplied shape similarity criteria (neighborhood distance) refer not to the whole query structure, but to its individual fragments. This allows the user to emphasize similarity to particular regions and features of his/her query structure, as may for example be suggested by consideration of X-ray structure or structure-activity tables. Therefore the method begins by assembling the lists of shape-similar synthons. The query structure is fragmented, either automatically in all reasonable ways as previously described or as the user may prescribe, and the topomeric shape with its descriptors is generated for each of these query fragments. Each of these topomeric fragments is then used as a query to search the synthon data base, producing its own list of shape-similar synthons.

In order to reduce needless computational overhead with its associated computational time, the shape similarity searches are accelerated by associating a heavy atom count with each synthon. The heavy atom count is a good reflection of the overall size of a molecular structure. If the heavy atom count of a query fragment differs by more than, typically, five atoms from the heavy atom count of a synthon, it is very unlikely that their topomeric shapes will be suitably similar; or put another way, the likelihood of the calculated topomeric distance being within the neighborhood distance is very low. This can be appreciated when one realizes that every additional atom in the synthon beyond those found in the query fragment, or vice versa, occupies an additional volume and will contribute additional field values within that volume that do not occur in the other. Such comparisons between two integers are of course very rapid and serve as a useful way of reducing the number of comparisons for which distance calculations need to be performed. The heavy atom difference may be specified by the user.

The lists of shape-similar synthons are also sub-divided according to the reactivity classifications of their open valences. The reasoning behind sub-diving the lists in this manner is that, when the synthons are combined into a putative molecule, the reactivity type at the open valence of each synthon must be complimentary to the reactivity type of the open valence of the other synthon. It is not necessary that a reaction be known between the first and second synthons since such a reaction may never have been reported in the literature. However, the requirement for complimentarity of reactivity type insures that incompatible molecular species are not suggested for the putative synthon molecule. Additional information is associated with each shape-similar synthon on a list, in particular its topomeric distance to the corresponding query fragment and the synthetic cost of producing the fragment. Note that the maximum topomeric distance for any synthon on any similarity list is equal to the user supplied criterion.

The lists are then grouped together in order to satisfy two further constraints on final product structures, first to regenerate correct correspondences to the query fragments and second to satisfy the requirement of mutual reactivity among the open valences of the synthons. Query correspondence is dealt with as follows. Assume a query structure whose acyclic single bonds allow its structure to be represented as A-B-C-D. The query fragmenter will then generate six fragmentations (A, B-C-D; A-B, C-D; A-B-C, D; A, B, C-D; A-B, C, D; A, B-C, D), yielding seven topomeric fragments (A, B, C, D, A-B, B-C, C-D). Each of these topomeric fragments will become a query into the synthon data base, yielding seven synthon lists as just described which can be denoted as (a, b, c, d, a-b, b-a, a-d). In order to satisfy the original query, these lists must be then be assembled to recreate the correspondences within query fragmentations, as follows: (a+b-c-d, a-b+c-d, a-b-c+d, a+b+cd, a-b+c+d, a+bc+d).

The second constraint, on the complementary reactivities of the open valences, must also be satisfied. For example, in a list assembly corresponding to a-b+c-d, it is possible that one subset of a-b's is electrophilic and another subset is nucleophilic. To satisfy the complementary reactivity requirement, this first a-b subset must then be grouped only with a c-d subset that is nucleophilic, and the second a-b only with a c-d subset that is electrophilic. Therefore, the assemblies of synthon lists must be further partitioned and rearranged. Of course, any resulting combinations that reference empty lists are immediately deleted. For example, if there are no shape similar nucleophilic c-d's, the reference to their combination with electrophilic a-b's will also be deleted. As a consequence of this list generation procedure, these partitioned and rearranged lists are now equivalent to selections resulting from a search of precomputed virtual libraries, exactly as for example as might have been produced by a topomer similarity search within a ChemSpace virtual library (U.S. Pat. No. 6,240,374). However, rather than being derived from reagents as was done in the formation of the ChemSpace virtual library, the synthons corresponding to the search queries have been created implicitly by the recursive synthon generator of this invention, and the lists are now created for consideration only as an outcome of the topomer search process itself. For convenience, these partitioned and rearranged lists are hereafter referred to as query-synthon shape selected lists (Q-SSSL).

Figure 16:
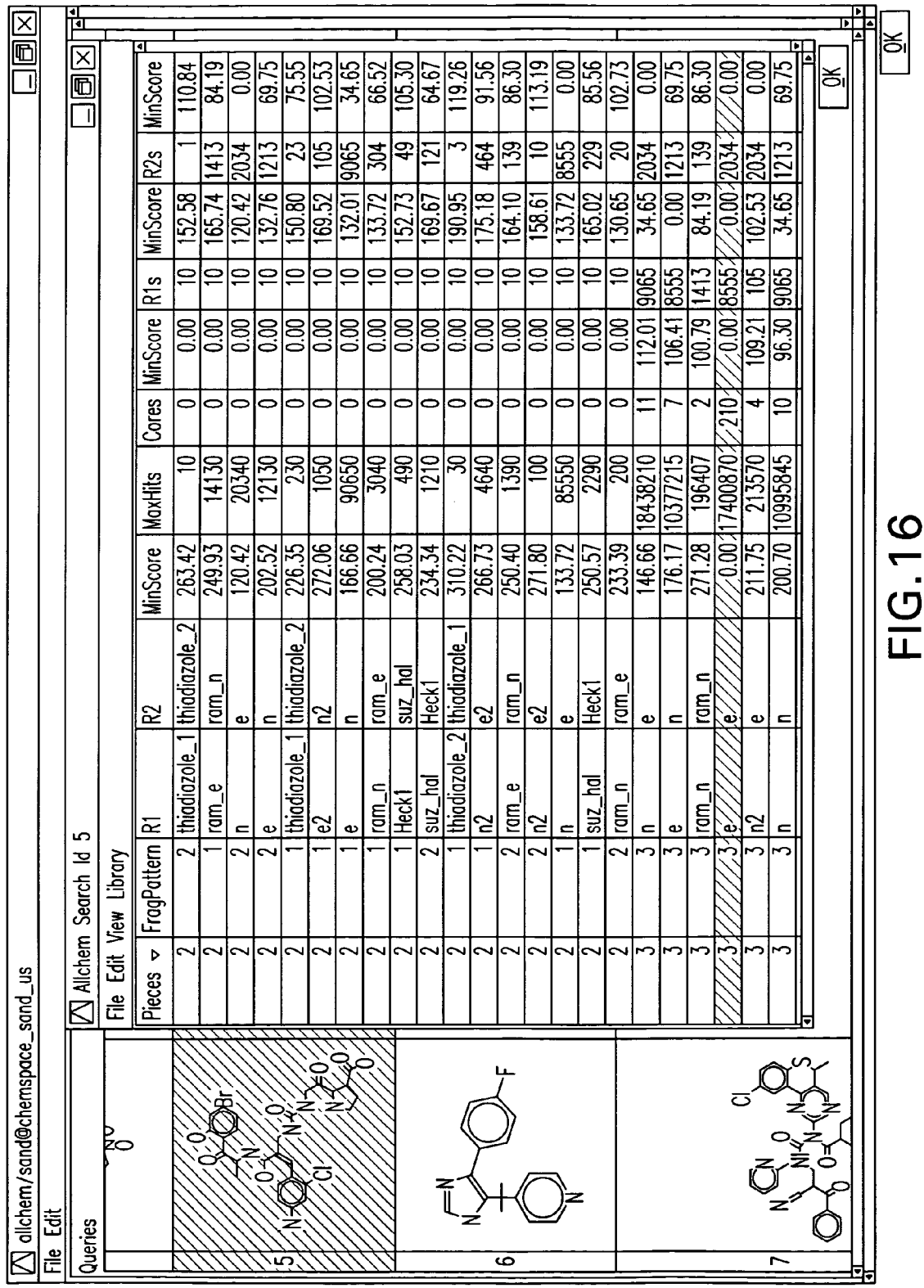
FIG. 16 shows a typical output of the list viewer of the invention.

These QSSSLs are now ready for their initial consideration by the user. The list viewer of this invention provides an output as seen in a exemplary screen shot shown in FIG. 16, as two overlaid spreadsheets. The underlying spreadsheet references all of a particular user's queries. The top spreadsheet contains the initial presentation of topomer similarity search results for the row highlighted within the underlying spreadsheet. Each row in the front spreadsheet corresponds to exactly one QSSSL selection. For example, consider the row immediately above the highlighted row. Its first "Pieces" column indicates that the QSSSL selection referenced by this row has three components. Continuing with the example above, these three components may correspond to one of three possible query fragmentations, a+b+cd, a-b+c+d, or a+bc+d. The particular correspondence for a row is then indicated by an arbitrary code value of 3 within the "FragPattern" column. (It can be noted that elsewhere in this column "FragPattern" code values of 1 and 2 denote two-piece fragmentations.) The side chains referenced by this row have reactivities of "ram_n" for "R1" and "ram_n" for "R2" (implying that all its cores will have open valences with complementary reactivities to "ram_n"). The most similar complete structure within this virtual library selection has a topomer distance of 271.28 ("MinScore" column)." There are a total of 196,407 products within this particular QSSSL selection, as appears in the "MaxHits column." There are 2 sufficiently shape similar cores noted in the "Cores" column, the most similar being 100.79 topomer units shape dissimilar from the core fragment of the query, when the query is fragmented according to "FragPattern" 3. There are 1413 candidate "R1s", the most similar being 84.19 topomer units dissimilar, with the open valences of these "R1s" as previously mentioned all having reactivity "ram_n", and there are 139 candidate "R2s", the most similar being 86.30 topomer units dissimilar, with the open valences of these "R1s as previously mentioned all having reactivity "ram_e". (It should be noted that this screen shot represents the state of a search result after some filtration of the products has occurred along the lines described below. If the screen shot instead represented an initial result, the "MaxHits" column would typically contain as the product of "Cores" times "R1s" times "R2s", a value greater than 2 million).

Accordingly, after initial compilation of the lists, the invention enables the user to utilize a variety of strategies for reducing this substantial collection of large QSSSLs to a much smaller set of compounds appropriate for synthesis and testing. For instance, the list viewer provides access to structures of at least some of the cores, the R1s, and the R2s, using the menu bar at the top of the spreadsheet to create paneled displays such as shown in FIGS. 12, 13, 14, and 15 that are described below. The reaction viewer described earlier provides access to the synthetic route that the recursive synthon generator used to propose a particular synthon, as exemplified in FIGS. 4, 5, and 6. Other computational filters implemented in the viewer include log P and molecular weight (drug transport properties), total synthetic cost of the individual synthons, reactivities of the synthons (affecting the difficulty of linking the synthons together), other forecasts of biological properties and similarity (such as docking or 2D fingerprints), Markush constraints (from the patent literature), and diversity based on all these criteria. The inventors believe that no other computational filtering environment exists that allows simultaneous consideration of both the (synthetic) costs and the prospective therapeutic benefit of a candidate structure. Of course, other subjective criteria, such as the synthetic chemist's personal experience with a particular reaction, will influence the final choice among candidate structures. All these choices and filters substantially reduce the number of synthons to be considered.

Examples of typical detailed outputs provided by the viewer of this invention are shown in the screen shots of FIGS. 12-15. The following example "walks through" the molecular structures in a manner similar to that which a chemist would use.

Figure 11:
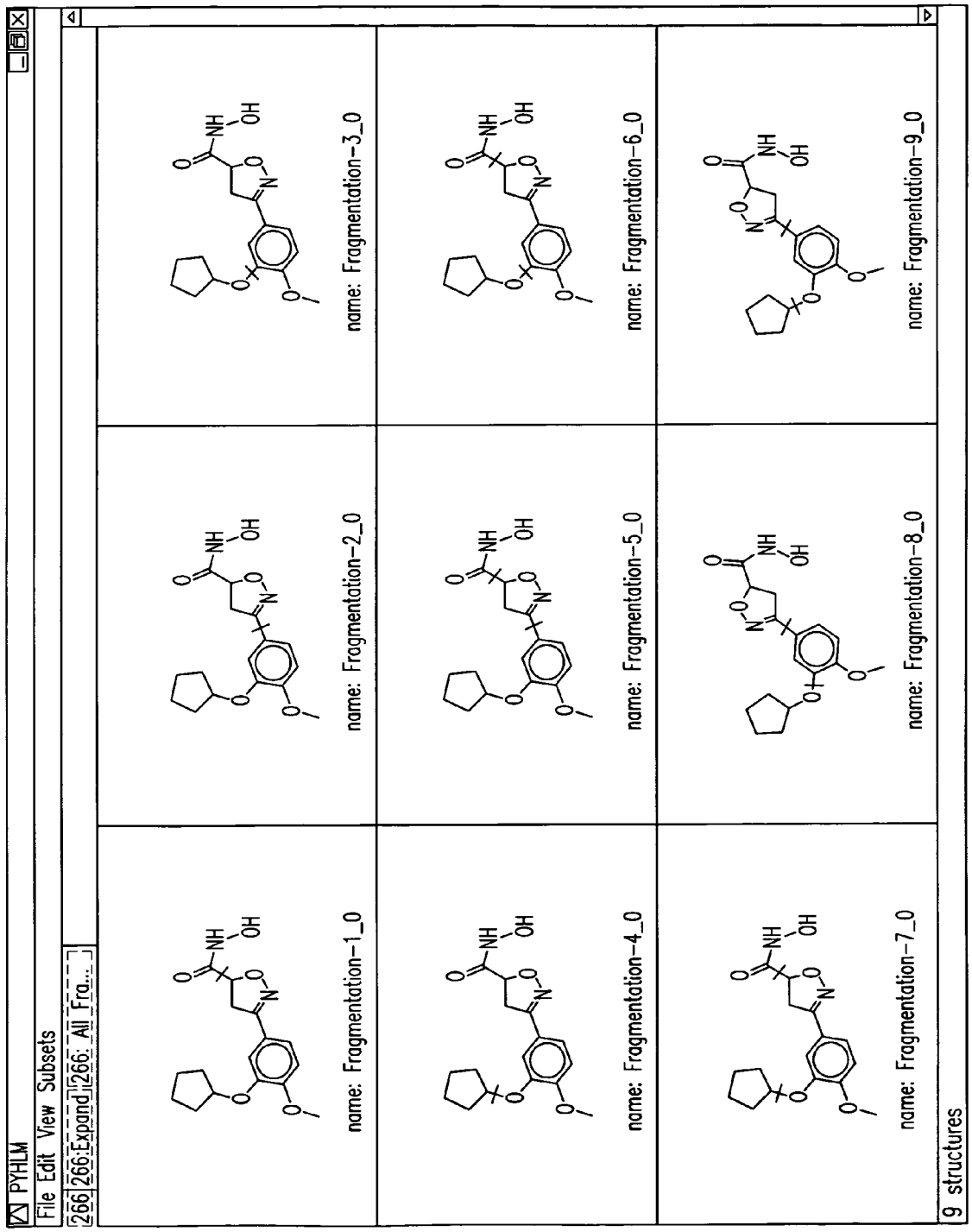
FIG. 11 illustrates the various way in which an example query molecule can be cut.

FIG. 11 illustrates the nine different ways in which the query molecule was fragmented. The bars across bonds represent that that bond was cut to create the fragments. Fragmentations 1-4 involve only a single bond and result in two part fragmentations. Fragmentations 5-9 involve two bonds being cut and result in a three part fragmentation. For this example, the fragmentation shown in Box 9 in the lower right hand corner is chosen as a starting point.

Figure 12:
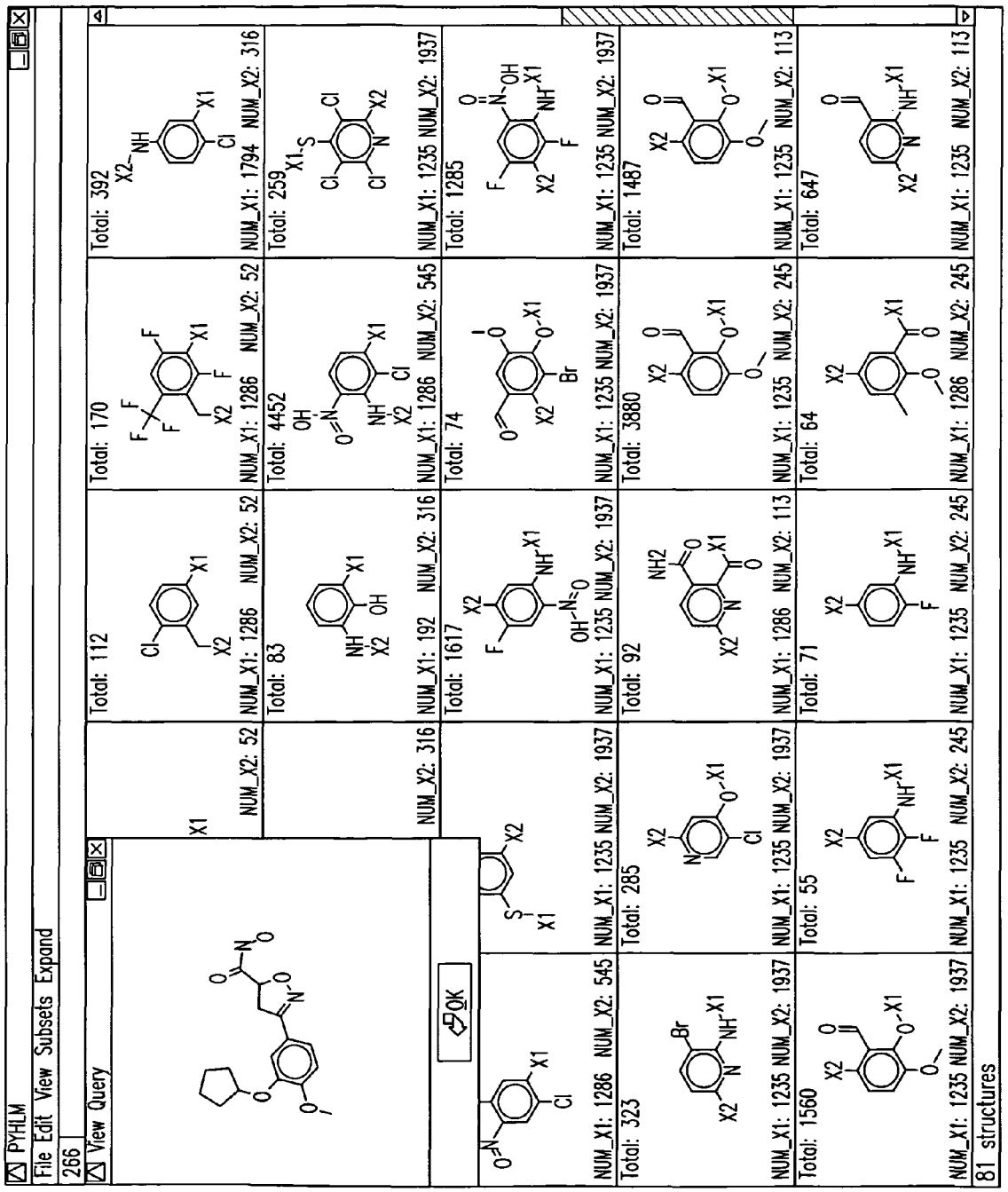
FIG. 12 shows the 25 representative synthons that are similar in shape and features to the divalent fragment of the query molecule generated by the fragmentation shown in Box No. 9 of FIG. 11.

In FIG. 12, the query molecule is shown in the boxed insert at the top left. Across the remainder of FIG. 12 are shown 25 representative synthons that are similar in shape and features to the divalent fragment of the query molecule generated by the fragmentation shown in Box 9 of FIG. 11. The total number of synthons (81) that met the neighborhood distance criteria of 110 set for this search is indicated in the lower left hand corner. Additional screens would show all 81 synthons.

Figure 13:
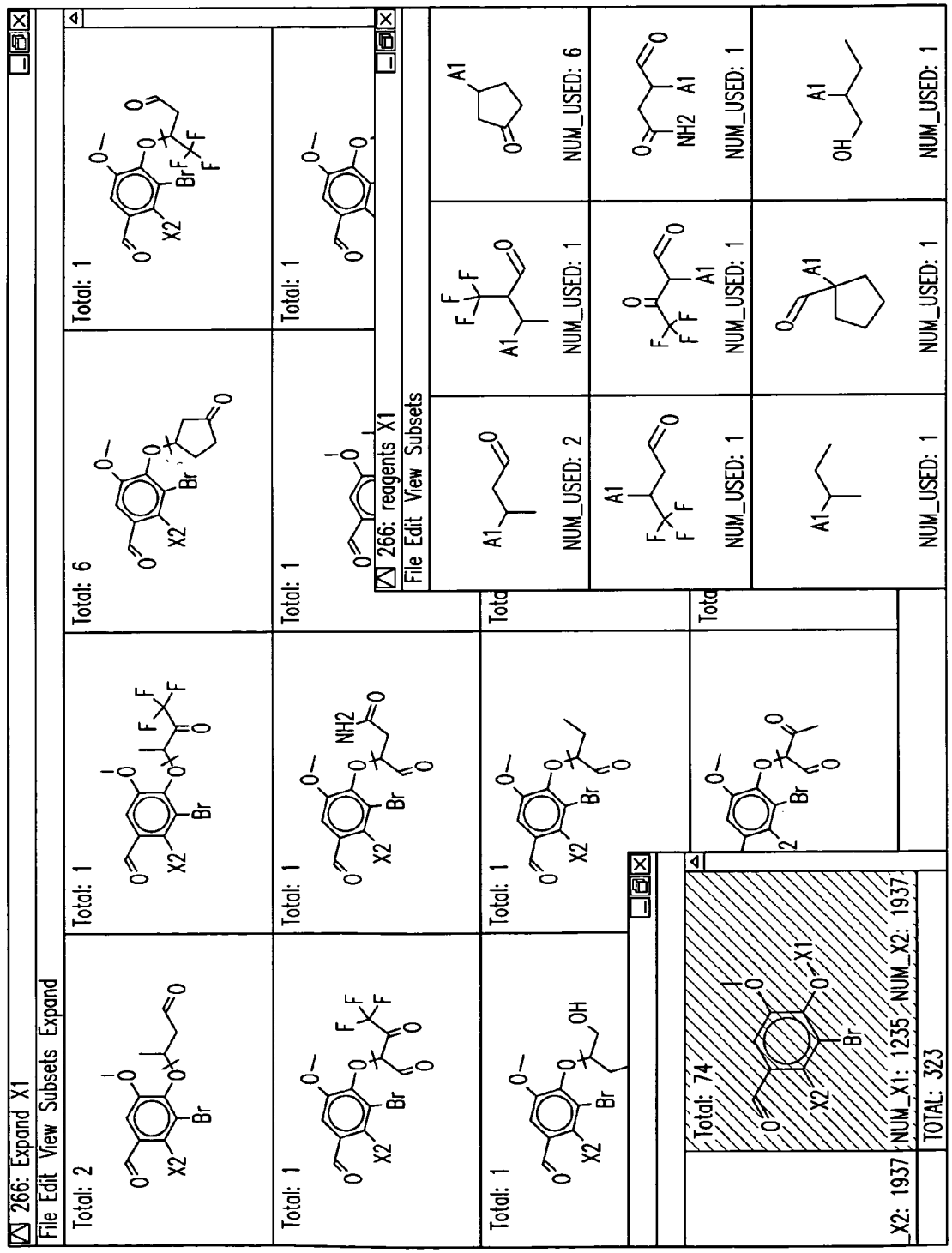
FIG. 13 shows the different structures that would result from combination of the synthon selected from row 3, column 4 of FIG. 12 with different side groups at the X1 position.
Figure 14:
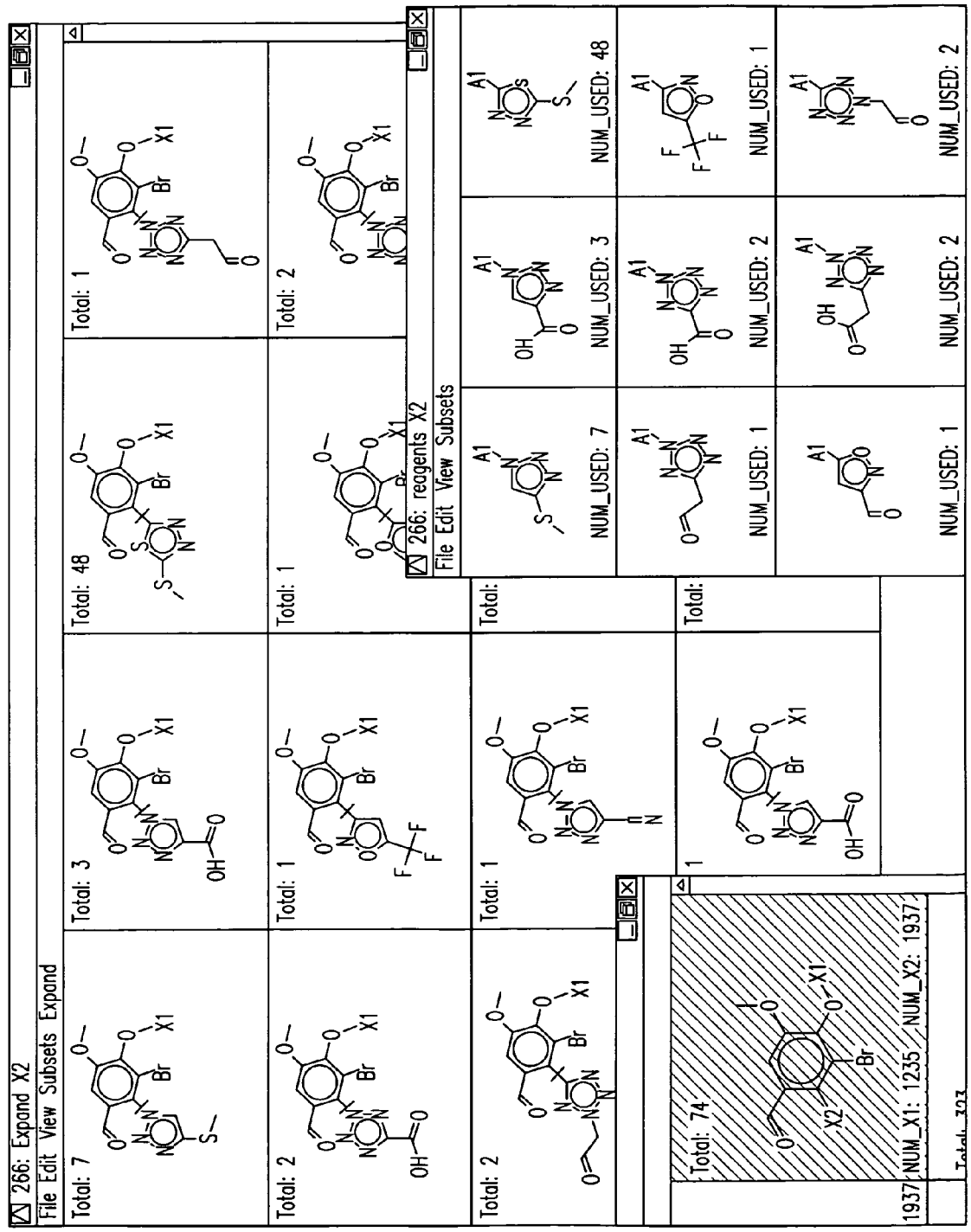
FIG. 14 shows the different structures that would result from combination of the synthon selected from row 3, column 4 of FIG. 12 with different side groups at the X2 position.

The synthon from row 3, column 4 of FIG. 12 has been chosen for further study in this example. FIG. 13 and FIG. 14 allow the chemist to explore the different structures that would result from combination of the synthon selected from row 3, column 4 of FIG. 12 with different side groups. In FIG. 13, that synthon is shown in the insert box in the lower left hand corner. The insert box on the lower right hand corner shows some representative synthons that were within the neighborhood cut off to be similar to the fragment of the initial query molecule located at the X1 position and that have the appropriate reactivity to combine at the X1 position. Behind the two insert boxes appear molecular structures generated by combining the synthons from the lower right hand box with the synthon from the lower left hand box at the X1 position.

Similarly, in FIG. 14, the synthon from row 3, column 4 of FIG. 12 is shown in the insert box in the lower left hand corner. The insert box on the lower right hand corner shows some representative synthons that were within the neighborhood cut off to be similar to the fragment of the initial query molecule located at the X2 position and that have the appropriate reactivity to combine at the X2 position. Behind the two insert boxes appear molecular structures generated by combining the synthons from the lower right hand box with the synthon from the lower left hand box at the X2 position.

Figure 15:
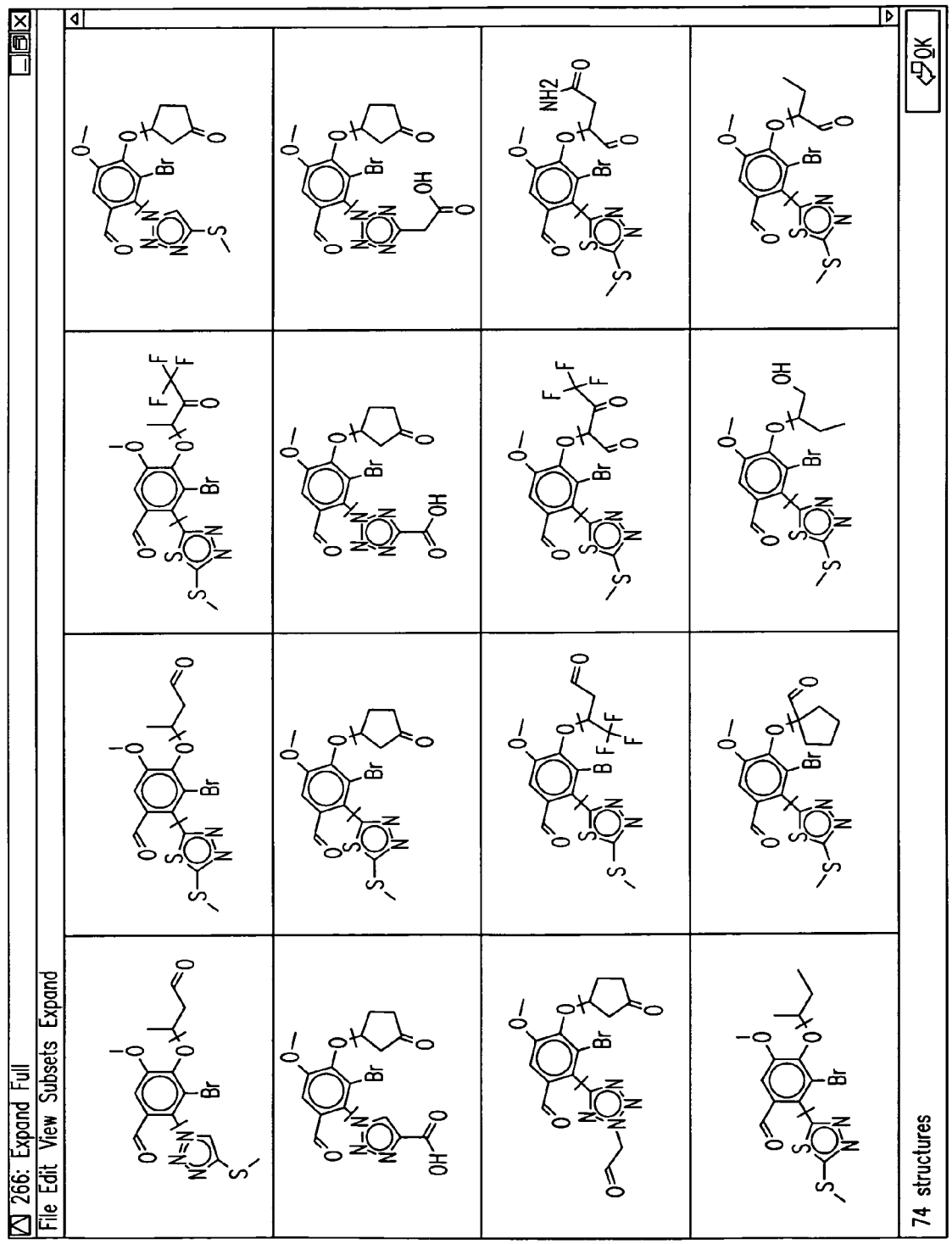
FIG. 15 shows the different structures that would result from combination of the synthon selected from row 3, column 4 of FIG. 12 with different side groups at both the X1 and X2 positions.

FIG. 15 shows a representative sample of the synthon combinations in which both the X1 and X2 positions have been filled. Clearly, not all synthon combinations are shown in any of these figures for combinations at the X1, X2, or X1 and X2 positions. The user can view all combinations on additional screens. In addition, the example shown in these figures highlight the possibilities for only one of the synthons shown in FIG. 13. The user may start with any of the 81 synthons identified in FIG. 13 and follow the same path to view possible X1, X2, and X1 and X2 combination molecular structures. In addition, the user can back up one more step and select a different fragmentation pattern from FIG. 12 to pursue in depth. Once all the synthon to fragment differences have been determined, the molecular structural data can be mined in many different ways and depths.

As noted earlier, for a variety of reasons a chemist may choose which structural path to follow depending on a number of factors. For example, a chemist interested in doing a "lead explosion" around a molecule with promising biological activity will wish to identify similarly shaped structures to his/her lead and may not be interested in similar shaped molecules derived from different chemistries as the lead. On the other hand, a chemist looking for a "lead hop" to a different chemistry would follow a path that yields topomerically similar but structurally distinct molecules. Most importantly, whatever path is followed, each of the resulting structures will be shape and feature similar to the query molecule within the user specified dissimilarity distance. Because a validated molecular metric was used to characterize the fragments and the synthons, the activity of the query molecule should be shared by the molecules resulting from combinations of identified synthons.

All functions of the synthetic reaction generator are fully enabled by the software code included in the software program appendix. Similarly, the analysis and output functions of the reaction viewer and list viewer are enabled by the software code included in the software program appendix. In the future, alternative outputs may be identified that might be useful for different types of searches.

The method of the present invention for the first time permits the generation of a rich and diverse universe of synthons derived from available starting materials by established synthetic pathways. When these synthons are used in three dimensional searching for those that have shapes similar to fragments of pharmacologically interesting molecules, new molecules are identified that are likely to have the same biological activity as the pharmacological molecule of interest. The method also provides for the identification of molecular structures having both similar shape and pharmacophoric properties. The identification of the shapes which contribute to the identified similarity provide an insight into the shape requirements of the receptor, and just as importantly, into likely additional molecular structures and corresponding shapes that will likely share the same activity. Thus, lead development is more straight forward from a knowledge of the relevant shape characteristics of the synthons provided by the method of this patent disclosure than from any two dimensional searching technique.

4. Future Advances From the proceeding description of the construction of a synthon generator and use of the resulting synthons for searching for shapes similar to query fragments, it should be clear that there are many variations which may be employed and, having taught how to generate and search in one specific embodiment, all equivalent embodiments are considered within the scope of this disclosure. While the preceding written description is provided as an aid in understanding the invention, it should be understood that the source code listings appended to this application constitute a complete disclosure of the best mode currently known to the inventors of the methods of synthon generation, searching, and output analysis and viewing.

G. Software Programs on CD-ROM Appendix

In addition to the software programs described as part of the computational environment specified in Section IV.A.1. above, the following software programs are required to practice the method of this invention and are incorporated into this patent document. These programs are set forth on the attached CD-ROM Appendix and are listed alphabetically by directory and subdirectory along with the file sizes and creation dates on the following pages:

| | | Viewer Code | |
|---|---|---|---|
| 03/26/2007 | 08:44p | <DIR> | . |
| 03/26/2007 | 08:44p | <DIR> | .. |
| 02/23/2007 | 05:20p | | 54,442 ac_database.py |
| 01/31/2007 | 04:00p | | 10,799 ac_design_viewer.py |
| 02/23/2007 | 05:17p | | 3,486 ac_hitlist.py |
| 02/22/2007 | 11:24a | | 18,791 ac_hitlist_viewer.py |
| 01/16/2007 | 03:14p | | 19,806 base.py |
| 02/19/2007 | 11:50a | | 3,814 ct_treemodel.py |
| 02/22/2007 | 01:43p | | 7,780 ct_utl.py |
| 11/20/2006 | 10:57a | | 18,516 file_dialog.py |
| 11/16/2006 | 02:29p | | 7,729 file_server.py |
| 11/16/2006 | 02:29p | | 6,157 filters.py |
| 02/19/2007 | 11:51a | | 17,666 grid.py |
| 11/16/2006 | 04:24p | | 7,253 hitlist_fields.py |
| 02/23/2007 | 05:16p | | 16,896 hitlist_viewer.py |
| 02/22/2007 | 03:22p | | 21,913 hitlists.py |
| 01/11/2007 | 11:05a | | 1,821 icons.py |
| 02/22/2007 | 03:36p | | 17,460 main.py |
| 02/14/2007 | 03:28p | | 5,187 main_menu.py |
| 11/27/2006 | 11:57a | | 34,143 matrix.py |
| 11/16/2006 | 02:29p | | 1,148 ora_db.py |
| 02/19/2007 | 11:48a | | 13,182 pp_bitmap.py |
| 03/22/2007 | 03:24p | | 247 README |
| 11/20/2006 | 02:09p | | 1,642 resources.py |
| 11/16/2006 | 02:29p | | 1,646 script_col.py |
| 11/16/2006 | 04:24p | | 26,025 sheet.py |
| 11/16/2006 | 02:29p | | 4,840 spreadsheet.py |

Viewer Code

| | | | |
|---|---|---|---|
| 01/12/2007 | 10:24a | 8,224 | statistics_table.py |
| 11/16/2006 | 03:20p | 10,657 | summary.py |
| 11/20/2006 | 02:11p | 7,530 | summary_dialog.py |
| 01/24/2007 | 10:34a | 49,159 | synth_dialog.py |
| 11/16/2006 | 03:16p | 30,565 | synth_eval.py |
| 12/04/2006 | 12:19p | 5,640 | synth_summary.py |
| 11/21/2006 | 01:11p | 16,828 | synth_tree.py |
| 11/21/2006 | 01:57p | 1,547 | toolbars.py |
| 11/16/2006 | 02:29p | 522 | util.py |
| 11/20/2006 | 02:12p | 40,783 | viewer_dialogs.py |
| 02/19/2007 | 11:50a | 31,321 | viewers.py |
| 02/07/2007 | 03:12p | 108,772 | vl.py |
| 12/15/2006 | 01:42p | 1,802 | vl_viewer.py |
| 11/16/2006 | 02:29p | 1,009 | winconfig.py |
| 11/16/2006 | 02:29p | 379 | winrun_ac_eval.py |
| 11/16/2006 | 02:29p | 352 | winrun_pyhlm.py |
| 11/16/2006 | 02:29p | 371 | winrun_synthesis.py |
| 11/20/2006 | 02:18p | 7,372 | workspace.py |

ALLCHEM CODE BY DIRECTORY AND SUBDIRECTORY

Allchem72
| | | | |
|---|---|---|---|
| 03/26/2007 | 08:44p | <DIR> | . |
| 03/26/2007 | 08:44p | <DIR> | .. |
| 03/26/2007 | 08:44p | <DIR> | ac_gen_frags |
| 03/26/2007 | 08:44p | <DIR> | ac_search_screen |
| 03/26/2007 | 08:44p | <DIR> | csbitset |
| 03/26/2007 | 08:44p | <DIR> | cshitlist |
| 03/26/2007 | 08:44p | <DIR> | dbcslnUtl |
| 03/26/2007 | 08:44p | <DIR> | scripts |
| 03/26/2007 | 08:44p | <DIR> | toputl |
| | 1 File(s) | 0 | bytes |

Allchem72\toputl
| | | | |
|---|---|---|---|
| 03/26/2007 | 08:44p | <DIR> | . |
| 03/26/2007 | 08:44p | <DIR> | .. |
| 03/26/2007 | 08:44p | <DIR> | include |
| 03/26/2007 | 08:44p | <DIR> | lib |
| 03/23/2007 | 01:59p | 158 | makefile |
| 03/26/2007 | 08:44p | <DIR> | source |
| | 1 File(s) | 158 | bytes |

Allchem72\toputl\source
| | | | |
|---|---|---|---|
| 03/26/2007 | 08:44p | <DIR> | . |
| 03/26/2007 | 08:44p | <DIR> | .. |
| 03/23/2007 | 01:59p | 8,252 | atomdist.c |
| 03/23/2007 | 01:59p | 5,173 | compresshex.c |
| 03/23/2007 | 01:59p | 13,719 | ct_chargeinit.c |
| 03/23/2007 | 01:59p | 17,809 | ct_chargeload.c |
| 03/23/2007 | 01:59p | 23,990 | ct_chargeutil.c |
| 03/23/2007 | 01:59p | 34,462 | ct_gasteiger.c |
| 03/23/2007 | 01:59p | 42,887 | ct_huckel.c |
| 03/23/2007 | 01:59p | 7,846 | ct_localright.c |
| 03/23/2007 | 01:59p | 84,424 | ct_topalign.c |
| 03/23/2007 | 01:59p | 38,717 | ct_topfeatures.c |
| 03/23/2007 | 01:59p | 33,088 | ct_topfield.c |
| 03/23/2007 | 01:59p | 63,325 | ex_utl.c |
| 03/23/2007 | 01:59p | 10,209 | gencoords.c |
| 03/23/2007 | 01:59p | 21,732 | ld_syb.c |
| 03/23/2007 | 01:59p | 14,637 | make.depend |
| 03/23/2007 | 01:59p | 1,978 | makefile |
| 03/23/2007 | 01:59p | 1,962 | makefile.70 |
| 03/23/2007 | 01:59p | 56,679 | split.c |
| 03/23/2007 | 01:59p | 9,711 | string.c |
| 03/23/2007 | 01:59p | 20,888 | tags |
| 03/23/2007 | 01:59p | 9,616 | top_utl.c |
| 03/23/2007 | 01:59p | 49,538 | top_utl_api_c.c |
| 03/23/2007 | 01:59p | 5,360 | Tri_I.c |
| | 23 File(s) | 576,002 | bytes |

Allchem72\toputl\lib
| | | | |
|---|---|---|---|
| 03/26/2007 | 08:44p | <DIR> | . |
| 03/26/2007 | 08:44p | <DIR> | .. |
| | File(s) | 0 | bytes |

ALLCHEM CODE BY DIRECTORY AND SUBDIRECTORY

Allchem72\toputl\include
| | | | |
|---|---|---|---|
| 03/26/2007 | 08:44p | <DIR> | . |
| 03/26/2007 | 08:44p | <DIR> | .. |
| 03/23/2007 | 01:59p | 478 | atomdist.h |
| 03/23/2007 | 01:59p | 121 | compresshex.h |
| 03/23/2007 | 01:59p | 398 | ct_chargeutil_proto.h |
| 03/23/2007 | 01:59p | 11,048 | ct_Tm2.h |
| 03/23/2007 | 01:59p | 5,828 | ct_top.h |
| 03/23/2007 | 01:59p | 948 | ct_topalign.h |
| 03/23/2007 | 01:59p | 560 | ct_topfeatures.h |
| 03/23/2007 | 01:59p | 1,036 | ct_topfield_proto.h |
| 03/23/2007 | 01:59p | 295 | gencoords.h |
| 03/23/2007 | 01:59p | 95 | localright.h |
| 03/23/2007 | 01:59p | 1,593 | split_control.h |
| 03/23/2007 | 01:59p | 6,602 | split_def.h |
| 03/23/2007 | 01:59p | 1,599 | split_proto.h |
| 03/23/2007 | 01:59p | 382 | string_p.h |
| 03/23/2007 | 01:59p | 1,077 | Tm2proto.h |
| 03/23/2007 | 01:59p | 3,974 | top_molecule.h |
| 03/23/2007 | 01:59p | 253 | top_utl.h |
| 03/23/2007 | 01:59p | 1,241 | top_utl_api.h |
| 03/23/2007 | 01:59p | 2,868 | top_utl_api_proto.h |
| 03/23/2007 | 01:59p | 452 | top_utl_p.h |
| 03/23/2007 | 01:59p | 3,544 | Tri_FF.h |
| 03/23/2007 | 01:59p | 1,211 | Tri_FF_p.h |
| | 22 File(s) | 45,603 | bytes |

Allchem72\scripts
| | | | |
|---|---|---|---|
| 03/26/2007 | 08:44p | <DIR> | . |
| 03/26/2007 | 08:44p | <DIR> | .. |
| 03/23/2007 | 01:58p | 147,667 | vl.py |
| | 1 File(s) | 147,667 | bytes |

Allchem72\dbcslnUtl
| | | | |
|---|---|---|---|
| 03/26/2007 | 08:44p | <DIR> | . |
| 03/26/2007 | 08:44p | <DIR> | .. |
| 03/23/2007 | 01:57p | 10,335 | ascii_file.c |
| 03/23/2007 | 01:57p | 178,658 | bitsetUtl.c |
| 03/23/2007 | 01:57p | 4,326 | commonData.c |
| 03/23/2007 | 01:57p | 42,653 | cs_ctchem.c |
| 03/23/2007 | 01:57p | 102,064 | db_oci.c |
| 03/23/2007 | 01:57p | 149,275 | dbcsln_hlm.c |
| 03/23/2007 | 01:57p | 136,898 | dbcsln_hlm.c.bak |
| 03/23/2007 | 01:57p | 55,548 | dbcsln_utl.c |
| 03/23/2007 | 01:57p | 7,557 | eliminate.c |
| 03/23/2007 | 01:57p | 65,583 | filter.c |
| 03/23/2007 | 01:57p | 5,115 | fingerPrint.c |
| 03/23/2007 | 01:57p | 83,880 | fred |
| 03/23/2007 | 01:57p | 11,045 | gen_utl.c |
| 03/23/2007 | 01:57p | 2,000 | m |
| 03/23/2007 | 01:57p | 0 | make.depend |
| 03/23/2007 | 01:57p | 2,140 | makefile |
| 03/23/2007 | 01:57p | 25,294 | prop_calc.c |
| 03/23/2007 | 01:57p | 70,620 | reagentclasses.lst |
| 03/23/2007 | 01:57p | 421 | sh_ctchem.h |
| 03/23/2007 | 01:57p | 2,383 | sh_ctchem_p.h |
| | 20 File(s) | 955,795 | bytes |

Allchem72\cshitlist
| | | | |
|---|---|---|---|
| 03/26/2007 | 08:44p | <DIR> | . |
| 03/26/2007 | 08:44p | <DIR> | .. |
| 03/23/2007 | 01:56p | 77,541 | cshitlistmodule.c |
| 03/23/2007 | 01:56p | 1,172 | make.depend |
| 03/23/2007 | 01:56p | 2,918 | makefile |
| 03/23/2007 | 01:56p | 2,289 | makefile.bak |
| 03/23/2007 | 01:56p | 121,684 | utl_bitmap.a |
| 03/23/2007 | 01:56p | 1,753 | utl_bitmap.h |
| | 6 File(s) | 207,357 | bytes |

Allchem72\csbitset
| | | | |
|---|---|---|---|
| 03/26/2007 | 08:44p | <DIR> | . |
| 03/26/2007 | 08:44p | <DIR> | .. |
| 03/26/2007 | 08:44p | <DIR> | include |
| 03/26/2007 | 08:44p | <DIR> | lib |
| 03/23/2007 | 01:58p | 303 | make.define |
| 03/23/2007 | 01:58p | 169 | makefile |
| 03/26/2007 | 08:44p | <DIR> | source |
| | 2 File(s) | 472 | bytes |

-continued

ALLCHEM CODE BY DIRECTORY AND SUBDIRECTORY

```
Allchem72\csbitset\source
03/26/2007  08:44p      <DIR>          .
03/26/2007  08:44p      <DIR>          ..
03/23/2007  01:58p          225,549    dbcsln_bs.c
03/23/2007  01:58p           69,158    ihbit.c
03/23/2007  01:58p           45,792    ihbit64.c
03/23/2007  01:58p            1,854    make.depend
03/23/2007  01:58p            1,639    makefile
03/23/2007  01:58p           29,997    masterUtl.c
03/23/2007  01:58p              166    test.hits
            7 File(s)       374,155    bytes
Allchem72\csbitset\lib
03/26/2007  08:44p      <DIR>          .
03/26/2007  08:44p      <DIR>          ..
            0 File(s)             0    bytes
Allchem72\csbitset\include
03/26/2007  08:44p      <DIR>          .
03/26/2007  08:44p      <DIR>          ..
03/23/2007  01:58p              211    cs_types.h
03/23/2007  01:58p              528    csln_type.h
03/23/2007  01:58p           10,152    dbcsln_bs_proto.h
03/23/2007  01:58p            2,333    ihbit_proto.h
03/23/2007  01:58p            4,397    masterUtl_proto.h
03/23/2007  01:58p              883    prop_col.h
            6 File(s)        18,504    bytes
Allchem72\ac_search_screen
03/26/2007  08:44p      <DIR>          .
03/26/2007  08:44p      <DIR>          ..
03/26/2007  08:44p      <DIR>          exe
03/26/2007  08:44p      <DIR>          include
03/26/2007  08:44p      <DIR>          lib
03/23/2007  01:56p              185    makefile
03/26/2007  08:44p      <DIR>          source
            1 File(s)           185    bytes
Allchem72\ac_search_screen\source
03/26/2007  08:44p      <DIR>          .
03/26/2007  08:44p      <DIR>          ..
03/23/2007  01:56p           52,929    ac_search.c
03/23/2007  01:56p              660    concord.log
03/23/2007  01:56p                0    coords.mol2
03/23/2007  01:56p            2,715    make.depend
03/23/2007  01:56p            2,024    makefile
03/23/2007  01:56p           74,298    oci_search.c
03/23/2007  01:56p           22,553    print_frags.c
            7 File(s)       155,179    bytes
Allchem72\ac_search_screen\lib
03/26/2007  08:44p      <DIR>          .
03/26/2007  08:44p      <DIR>          ..
            0 File(s)             0    bytes
Allchem72\ac_search_screen\include
03/26/2007  08:44p      <DIR>          .
03/26/2007  08:44p      <DIR>          ..
03/23/2007  01:56p            3,095    ac_search.h
03/23/2007  01:56p            1,339    oci_search.h
            2 File(s)         4,434    bytes
Allchem72\ac_search_screen\exe
03/26/2007  08:44p      <DIR>          .
03/26/2007  08:44p      <DIR>          ..
03/23/2007  01:56p            8,451    main.c
03/23/2007  01:56p              718    make.depend
03/23/2007  01:56p            2,355    makefile
            3 File(s)        11,524    bytes
Allchem72\ac_gen_frags
03/26/2007  08:44p      <DIR>          .
03/26/2007  08:44p      <DIR>          ..
03/23/2007  01:56p           12,048    ac_gen_frags.c
03/23/2007  01:56p            2,425    ac_gen_frags.h
03/23/2007  01:56p              660    concord.log
03/23/2007  01:56p            3,185    convertA1.c
03/23/2007  01:56p                0    coords.mol2
03/23/2007  01:56p            2,095    main.c
03/23/2007  01:56p            3,924    make.depend
03/23/2007  01:56p            3,048    makefile
03/23/2007  01:56p           53,393    oci_gen_frags.c
03/23/2007  01:56p               78    oci_gen_frags.h
03/23/2007  01:56p           32,788    utl_mem.c
```

V. REFERENCES

1. Weininger, D., Encycl. Comp. Chem. 1998, 1, 425-430.
2. Todd, M. H. Computer-aided organic synthesis. Chem. Soc. Rev., 2005, 34, 247-266.
3. Cramer, R. D. Topomer CoMFA: A Design Methodology for Rapid Lead Optimization, J. Med. Chem. 2003, 46, 374-389.
4. Nicolaou, K. C., Hanko, R., Hartwig, R. Handbook of Combinatorial Chemistry. Wiley-VCH, Weinheim, Germany. 2002 (two volumes).
5. Ash S., Cline, M. A., Horner, R. W., Hurst, T., Smith, G. B. SYBYL line notation (SLN): A versatile language for chemical structure representation. J. Chem. Inf. Comput. Sci. 1997, 37, 71-79.
6. In practice, known stereocenters are treated no differently from unknown stereocenters, which seems paradoxical for a methodology addressing shape similarity. The reason is that topomeric similarity is always being assessed within a context where far more stereoforms are unknown than known. Whether a fragment structure is part of a query or a potentially matching fragment, because the far more numerous unassigned stereoforms will always have been standardized topomerically, any known stereocenter has a roughly 50% chance of being the non-topomeric stereoisomer. As a result, structurally identical fragments would be topomerically dissimilar and unrecognized 50% of the time. Faced with this very unattractive outcome, it was agreed that known stereocenters would be structurally registered but ignored in topomer modeling. Racemic fragments thus become two distinct registered "substances" mapping to the same topomer.
7. Two atoms or groups that upon replacement with a third group give enantiomers are denoted as "enantiotopic". March, J. *Advanced Organic Chemistry, Reactions, Mechanisms, and Structure;* 4$^{th}$ edition, John Wiley, NYC, 1991; p. 135.

We claim:

1. A computer implemented method utilizing a specifically programmed computer of generating the structures of new synthons using the molecular structures of available starting materials and known chemical reactions comprising the steps of:
   a. inputting definitions of available starting materials;
   b. defining reactions;
   c. applying a recursive forward synthesis synthon generator to identify the structures of new synthons;
   d. outputting the results.

2. A computer implemented method utilizing a specifically programmed computer for generating molecular fragments possessing an open valence through recursive application of established synthetic pathways comprising the steps of:
   (a) defining established synthetic reactions and the synthetic cost associated with each reaction;
   (b) establishing rules for the application of the synthetic reactions to reagents or fragments;
   (c) inputting the molecular structure of available reagents;
   (d) selecting a reagent;
   (e) using the established rules, apply all synthetic reactions to the reagent that:
      (1) do not result in an intermediate with a heavy atom count that exceeds a defined threshold; and
      (2) do not result in a total synthetic cost that exceeds a defined threshold; and
      (3) do not result in an intermediate with a number of chiral centers that exceeds a defined threshold; and (f) outputting to a database listing, that may be reviewed by a user, the intermediates that result from reactions in step (e) along with the associated synthetic cost that generated each intermediate;

(g) using the established rules, apply all reactions to all intermediates in the database listing that:
  (1) do not result in an intermediate with a heavy atom count that exceeds a defined threshold; and
  (2) do not result in a total synthetic cost that exceeds a defined threshold; and
  (3) do not result in an intermediate with a number of chiral centers that exceeds a defined threshold;

(h) outputting to the database listing, that may be reviewed by a user, intermediates that are not already in the database that result from reactions in step (g) along with the associated synthetic cost that generated each intermediate;

(i) repeating steps (g) through (h) until no more unique intermediates are generated; and (j) repeating steps (d) through (i) until all reagents have been processed.

3. The method of claim 2 wherein in steps (f) and (h) the reactions that yielded the intermediates are additionally output.

4. The method of claim 3 wherein in steps (f) and (h) the reactions that generated intermediates identical to ones previously listed in the database are associated with the intermediates as alternative synthetic reactions.

5. A computer implemented method utilizing a specifically programmed computer for generating molecular fragments possessing an open valence through recursive application of established synthetic pathways comprising the steps of:

(a) defining established synthetic reactions and the synthetic cost associated with each reaction;

(b) establishing rules for the application of the synthetic reactions to reagents or fragments;

(c) inputting the molecular structure of available reagents;

(d) selecting a reagent;

(e) using the established rules, apply all synthetic reactions to the reagent that do not result in an intermediate with a number of chiral centers that exceeds a defined threshold; and (f) outputting to a database listing, that may be reviewed by a user, the intermediates that result from reactions in step (e);

(g) using the established rules, apply all reactions to all intermediates in the database listing that do not result in an intermediate with a number of chiral centers that exceeds a defined threshold;

(h) outputting to the database listing, that may be reviewed by a user, intermediates that are not already in the database that result from reactions in step (g);

(i) repeating steps (g) through (h) until no more unique intermediates are generated; and (j) repeating steps (d) through (i) until all reagents have been processed.

6. The method of claim 5 wherein in steps (f) and (h) the reactions that yielded the intermediates are additionally output.

7. The method of claim 6 wherein in steps (f) and (h) the reactions that generated intermediates identical to ones previously listed in the database are associated with the intermediates as alternative synthetic reactions.

8. A computer implemented method utilizing a specifically programmed computer for generating molecular fragments possessing an open valence through recursive application of established synthetic pathways comprising the steps of:

(a) defining established synthetic reactions and the synthetic cost associated with each reaction;

(b) establishing rules for the application of the synthetic reactions to reagents or fragments;

(c) inputting the molecular structure of available reagents;

(d) selecting a reagent;

(e) using the established rules, apply all synthetic reactions to the reagent that do not result in a total synthetic cost that exceeds a defined threshold; and (f) outputting to a database listing, that may be reviewed by a user, the intermediates that result from reactions in step (e) along with the associated synthetic cost that generated each intermediate;

(g) using the established rules, apply all reactions to all intermediates in the database listing that do not result in a total synthetic cost that exceeds a defined threshold; and (h) outputting to the database listing, that may be reviewed by a user, intermediates that are not already in the database that result from reactions in step (g) along with the associated synthetic cost that generated each intermediate;

(i) repeating steps (g) through (h) until no more unique intermediates are generated; and (j) repeating steps (d) through (i) until all reagents have been processed.

9. The method of claim 8 wherein in steps (f) and (h) the reactions that yielded the intermediates are additionally output.

10. The method of claim 9 wherein in steps (f) and (h) the reactions that generated intermediates identical to ones previously listed in the database are associated with the intermediates as alternative synthetic reactions.

11. A computer implemented method utilizing a specifically programmed computer for generating molecular fragments possessing an open valence through recursive application of established synthetic pathways comprising the steps of:

(a) defining established synthetic reactions and the synthetic cost associated with each reaction;

(b) establishing rules for the application of the synthetic reactions to reagents or fragments;

(c) inputting the molecular structure of available reagents;

(d) selecting a reagent;

(e) using the established rules, apply all synthetic reactions to the reagent that do not result in an intermediate with a heavy atom count that exceeds a defined threshold; and (f) outputting to a database listing, that may be reviewed by a user, the intermediates that result from reactions in step (e);

(g) using the established rules, apply all reactions to all intermediates in the database listing that do not result in an intermediate with a heavy atom count that exceeds a defined threshold; and (h) outputting to the database listing, that may be reviewed by a user, intermediates that are not already in the database that result from reactions in step (g);

(i) repeating steps (g) through (h) until no more unique intermediates are generated; and (j) repeating steps (d) through (i) until all reagents have been processed.

12. The method of claim 11 wherein in steps (f) and (h) the reactions that yielded the intermediates are additionally output.

13. The method of claim 12 wherein in steps (f) and (h) the reactions that generated intermediates identical to ones previously listed in the database are associated with the intermediates as alternative synthetic reactions.

14. A computer implemented method utilizing a specifically programmed computer for generating molecular fragments possessing an open valence through recursive application of established synthetic pathways comprising the steps of:
   (a) defining established synthetic reactions and the synthetic cost associated with each reaction;
   (b) establishing rules for the application of the synthetic reactions to reagents or fragments;
   (c) inputting the molecular structure of available reagents;
   (d) selecting a reagent;
   (e) using the established rules, apply all synthetic reactions to the reagent that:
      (1) do not result in a total synthetic cost that exceeds a defined threshold; and
      (2) do not result in an intermediate with a number of chiral centers that exceeds a defined threshold; and
   (f) outputting to a database listing, that may be reviewed by a user, the intermediates that result from reactions in step (e) along with the associated synthetic cost that generated each intermediate;
   (g) using the established rules, apply all reactions to all intermediates in the database listing that:
      (1) do not result in a total synthetic cost that exceeds a defined threshold; and
      (2) do not result in an intermediate with a number of chiral centers that exceeds a defined threshold; and
   (h) outputting to the database listing, that may be reviewed by a user, intermediates that are not already in the database that result from reactions in step (g) along with the associated synthetic cost that generated each intermediate;
   (i) repeating steps (g) through (h) until no more unique intermediates are generated; and
   (j) repeating steps (d) through (i) until all reagents have been processed.

15. The method of claim 14 wherein in steps (f) and (h) the reactions that yielded the intermediates are additionally output.

16. The method of claim 15 wherein in steps (f) and (h) the reactions that generated intermediates identical to ones previously listed in the database are associated with the intermediates as alternative synthetic reactions.

17. A computer implemented method utilizing a specifically programmed computer for generating molecular fragments possessing an open valence through recursive application of established synthetic pathways comprising the steps of:
   (a) defining established synthetic reactions and the synthetic cost associated with each reaction;
   (b) establishing rules for the application of the synthetic reactions to reagents or fragments;
   (c) inputting the molecular structure of available reagents;
   (d) selecting a reagent;
   (e) using the established rules, apply all synthetic reactions to the reagent that:
      (1) do not result in an intermediate with a heavy atom count that exceeds a defined threshold; and
      (2) do not result in an intermediate with a number of chiral centers that exceeds a defined threshold; and
   (f) outputting to a database listing, that may be reviewed by a user, the intermediates that result from reactions in step (e);
   (g) using the established rules, apply all reactions to all intermediates in the database listing that:
      (1) do not result in an intermediate with a heavy atom count that exceeds a defined threshold; and
      (2) do not result in an intermediate with a number of chiral centers that exceeds a defined threshold; and
   (h) outputting to the database listing, that may be reviewed by a user, intermediates that are not already in the database that result from reactions in step (g);
   (i) repeating steps (g) through (h) until no more unique intermediates are generated; and
   (j) repeating steps (d) through (i) until all reagents have been processed.

18. The method of claim 17 wherein in steps (f) and (h) the reactions that yielded the intermediates are additionally output.

19. The method of claim 18 wherein in steps (f) and (h) the reactions that generated intermediates identical to ones previously listed in the database are associated with the intermediates as alternative synthetic reactions.

20. A computer implemented method utilizing a specifically programmed computer for generating molecular fragments possessing an open valence through recursive application of established synthetic pathways comprising the steps of:
   (a) defining established synthetic reactions and the synthetic cost associated with each reaction;
   (b) establishing rules for the application of the synthetic reactions to reagents or fragments;
   (c) inputting the molecular structure of available reagents;
   (d) selecting a reagent;
   (e) using the established rules, apply all synthetic reactions to the reagent that:
      (1) do not result in an intermediate with a heavy atom count that exceeds a defined threshold; and
      (2) do not result in a total synthetic cost that exceeds a defined threshold; and
   (f) outputting to a database listing, that may be reviewed by a user, the intermediates that result from reactions in step (e) along with the associated synthetic cost that generated each intermediate;
   (g) using the established rules, apply all reactions to all intermediates in the database listing that:
      (1) do not result in an intermediate with a heavy atom count that exceeds a defined threshold; and
      (2) do not result in a total synthetic cost that exceeds a defined threshold; and
   (h) outputting to the database listing, that may be reviewed by a user, intermediates that are not already in the database that result from reactions in step (g) along with the associated synthetic cost that generated each intermediate;
   (i) repeating steps (g) through (h) until no more unique intermediates are generated; and
   (j) repeating steps (d) through (i) until all reagents have been processed.

21. The method of claim 20 wherein in steps (f) and (h) the reactions that yielded the intermediates are additionally output.

22. The method of claim 21 wherein in steps (f) and (h) the reactions that generated intermediates identical to ones previously listed in the database are associated with the intermediates as alternative synthetic reactions.

23. A computer implemented method utilizing a specifically programmed computer for generating molecular fragments possessing an open valence through recursive application of established synthetic pathways comprising the steps of:

(a) defining established synthetic reactions and the synthetic cost associated with each reaction;
(b) establishing rules for the application of the synthetic reactions to reagents or fragments;
(c) inputting the molecular structure of available reagents;
(d) selecting a reagent;
(e) using the established rules, apply all synthetic reactions to the reagent that:
  (1) do not result in an intermediate with a heavy atom count that exceeds a defined threshold; and
  (2) do not result in a total synthetic cost that exceeds a defined threshold; and
  (3) do not result in an intermediate with a number of chiral centers that exceeds a defined threshold; and
(f) outputting to a database listing, that may be reviewed by a user, the intermediates that result from reactions in step (e) along with the associated synthetic cost that generated each intermediate;
(g) using the established rules, apply all reactions to all intermediates in the database listing that:
  (1) do not result in an intermediate with a heavy atom count that exceeds a defined threshold; and
  (2) do not result in a total synthetic cost that exceeds a defined threshold; and
  (3) do not result in an intermediate with a number of chiral centers that exceeds a defined threshold;
(h) outputting to the database listing, that may be reviewed by a user, intermediates that are not already in the database that result from reactions in step (g) along with the associated synthetic cost that generated each intermediate;
(i) repeating steps (g) through (h) until no more unique intermediates are generated;
(j) repeating steps (d) through (i) until all reagents have been processed;
(k) using the established rules, apply all reactions to all combinations of intermediates in the database listing that:
  (1) do not result in an intermediate with a heavy atom count that exceeds a defined threshold; and
  (2) do not result in a total synthetic cost that exceeds a defined threshold; and
  (3) do not result in an intermediate with a number of chiral centers that exceeds a defined threshold; and
(l) outputting to the database listing, that may be reviewed by a user, intermediates that are not already in the database that result from reactions in step (k) along with the associated synthetic cost that generated each intermediate.

24. The method of claim 23 wherein in steps (f), (h), and (l) the reactions that yielded the intermediates are additionally output.

25. The method of claim 24 wherein in steps (f) and (h) the reactions that generated intermediates identical to ones previously listed in the database are associated with the intermediates as alternative synthetic reactions.

26. A computer implemented method utilizing a specifically programmed computer for generating molecular fragments possessing an open valence through recursive application of established synthetic pathways comprising the steps of:
(a) defining established synthetic reactions and the synthetic cost associated with each reaction;
(b) establishing rules for the application of the synthetic reactions to reagents or fragments;
(c) inputting the molecular structure of available reagents;
(d) selecting a reagent;
(e) using the established rules, apply all synthetic reactions to the reagent that result in intermediates meeting specified limitations;
(f) outputting to a database listing, that may be reviewed by a user, the intermediates that result from reactions in step (e);
(g) using the established rules, apply all reactions to all intermediates in the database listing that result in intermediates meeting specified limitations:
(h) outputting to the database listing, that may be reviewed by a user, intermediates that are not already in the database that result from reactions in step (g);
(i) repeating steps (g) through (h) until no more unique intermediates are generated; and
(j) repeating steps (d) through (i) until all reagents have been processed.

27. A system for identifying molecular structures similar in three dimensional shape and likely to have the same biological activity as a known pharmacologically active query molecule comprising:
(A) generating synthons possessing an open valence through recursive application of established synthetic pathways comprising the steps of:
  (1) defining established synthetic reactions and the synthetic cost associated with each reaction;
  (2) establishing rules for the application of the synthetic reactions to reagents or fragments;
  (3) inputting the molecular structure of available reagents;
  (4) selecting a reagent;
  (5) using the established rules, apply all synthetic reactions to the reagent that:
    (a) do not result in an intermediate with a heavy atom count that exceeds a defined threshold; and
    (b) do not result in a total synthetic cost that exceeds a defined threshold; and
    (c) do not result in an intermediate with a number of chiral centers that exceeds a defined threshold; and
  (6) outputting to a database listing, that may be reviewed by a user, the intermediates that result from reactions in step (5) along with the reaction and its associated synthetic cost that generated each intermediate;
  (7) using the established rules, apply all reactions to all intermediates in the database listing that:
    (a) do not result in an intermediate with a heavy atom count that exceeds a defined threshold; and
    (b) do not result in a total synthetic cost that exceeds a defined threshold; and
    (c) do not result in an intermediate with a number of chiral centers that exceeds a defined threshold;
  (8) outputting to the database listing, that may be reviewed by a user;
    (a) intermediates that are not already in the database that result from reactions in step (7) along with the reaction and its associated synthetic cost that generated each intermediate;
    (b) reactions used in step (7) that generate intermediates identical to ones previously listed in the database and are associated with the identical intermediates as alternative synthetic reactions;
  (9) repeating steps (7) through (8) until no more unique intermediates are generated; and
  (10) repeating steps (4) through (9) until all reagents have been processed; and (B) characterizing synthons comprising the steps of:
  (1) topomerically aligning the synthons to generate a topomeric conformation for each;
  (2) generating the interaction energies between a probe and the atoms in each topomerically aligned synthon at all intersection points in a three dimensional grid surrounding each aligned synthon and storing the field values for each synthon in the database;
  (3) storing the reactivity type for each synthon in the database;
(C) characterizing the query molecule comprising the steps of:
  (1) fragmenting the query molecule according to a defined set of rules;
  (2) topomerically aligning the fragments to generate a topomeric conformation for each;
  (3) generating the interaction energies between a probe and the atoms in each topomerically aligned fragment at all intersection points in a three dimensional grid surrounding each aligned synthon and storing the field values for each fragment in the database;
  (4) storing the reactivity type for each fragment in the database;
(D) identifying the synthons that are most similar to the query fragments comprising the steps of:
  (1) determining the shape similarity between query fragments and synthons by the root sum of square differences in the characterizing field values with smaller differences in field values indicating greater similarity;
  (2) determining which of the similarly shaped synthons have the same reactivity type as the query fragments to which they are most shape similar;
(E) outputting the molecules formed from combinations of synthons that result from substitution of synthons for similarly shaped query fragments having the same reactivity type.

* * * * *